US009404916B2

(12) United States Patent
Sewell et al.

(10) Patent No.: US 9,404,916 B2
(45) Date of Patent: Aug. 2, 2016

(54) USE OF A PROTEIN KINASE INHIBITOR TO DETECT IMMUNE CELLS, SUCH AS T CELLS

(75) Inventors: Andrew Kelvin Sewell, Cardiff (GB); Linda Wooldridge, Bridgend (GB)

(73) Assignee: University College Cardiff Consultants Limited, Cardiff (GB)

( * ) Notice: Subject to any disclaimer, the term of this patent is extended or adjusted under 35 U.S.C. 154(b) by 327 days.

(21) Appl. No.: 13/119,795

(22) PCT Filed: Sep. 18, 2009

(86) PCT No.: PCT/GB2009/002251
§ 371 (c)(1),
(2), (4) Date: Apr. 25, 2011

(87) PCT Pub. No.: WO2010/032022
PCT Pub. Date: Mar. 25, 2010

(65) Prior Publication Data
US 2011/0195435 A1    Aug. 11, 2011

(30) Foreign Application Priority Data
Sep. 20, 2008 (GB) .................. 0817244.7

(51) Int. Cl.
*G01N 33/49*    (2006.01)
*G01N 33/50*    (2006.01)
*G01N 33/543*    (2006.01)

(52) U.S. Cl.
CPC ........ *G01N 33/505* (2013.01); *G01N 33/54393* (2013.01)

(58) Field of Classification Search
None
See application file for complete search history.

(56) References Cited

U.S. PATENT DOCUMENTS

| 4,336,173 A | 6/1982 | Ugelstad |
| 4,387,164 A | 6/1983 | Hevey et al. |
| 4,459,378 A | 7/1984 | Ugelstad |
| 4,654,267 A | 3/1987 | Ugelstad et al. |
| 4,876,190 A | 10/1989 | Recktenwald |
| 5,039,487 A | 8/1991 | Smith |
| 5,130,297 A | 7/1992 | Sharma et al. |
| 5,194,425 A | 3/1993 | Sharma et al. |
| 5,260,422 A | 11/1993 | Clark et al. |
| 5,284,935 A | 2/1994 | Clark et al. |
| 5,312,744 A | 5/1994 | Shibata |
| 5,468,481 A | 11/1995 | Sharma et al. |
| 5,583,031 A | 12/1996 | Stern |
| 5,627,037 A | 5/1997 | Ward et al. |
| 5,635,363 A | 6/1997 | Altman et al. |
| 5,652,342 A | 7/1997 | Zimmerman et al. |
| 5,807,552 A | 9/1998 | Stanton et al. |
| 5,869,270 A | 2/1999 | Rhode et al. |
| 5,891,741 A | 4/1999 | Siiman et al. |
| 5,955,079 A | 9/1999 | Mond et al. |
| 5,994,089 A | 11/1999 | Siiman et al. |
| 5,998,204 A | 12/1999 | Tsien et al. |
| 6,015,884 A | 1/2000 | Schneck et al. |
| 6,074,645 A | 6/2000 | Diamond et al. |
| 6,090,587 A | 7/2000 | Rhodes et al. |
| 6,096,315 A | 8/2000 | Zimmerman et al. |
| 6,106,840 A | 8/2000 | Clark et al. |
| 6,129,916 A | 10/2000 | Chang |
| 6,140,113 A | 10/2000 | Schneck et al. |
| 6,156,317 A | 12/2000 | Diamond et al. |
| 6,156,514 A | 12/2000 | Acevedo et al. |
| 6,197,302 B1 | 3/2001 | Hirsch et al. |
| 6,197,928 B1 | 3/2001 | Tsien et al. |
| 6,211,342 B1 | 4/2001 | Hirsch et al. |
| 6,232,445 B1 | 5/2001 | Rhode et al. |
| 6,248,564 B1 | 6/2001 | Walter et al. |
| 6,251,399 B1 | 6/2001 | Diamond et al. |
| 6,268,411 B1 | 7/2001 | Schneck et al. |
| 6,306,605 B1 | 10/2001 | Acevedo et al. |
| 6,309,645 B1 | 10/2001 | Rhode et al. |
| 6,335,173 B1 | 1/2002 | Kaplan |
| 6,387,622 B1 | 5/2002 | Siiman et al. |
| 6,448,071 B1 | 9/2002 | Schneck et al. |
| 6,451,314 B1 | 9/2002 | Clark et al. |
| 6,451,769 B1 | 9/2002 | Huebner et al. |
| 6,458,354 B1 | 10/2002 | Schneck et al. |
| 6,458,933 B1 | 10/2002 | Hansen |
| 6,486,130 B1 | 11/2002 | Livey et al. |
| 6,534,633 B1 | 3/2003 | Weidanz et al. |
| 6,548,067 B1 | 4/2003 | Seeman et al. |
| 6,734,013 B2 | 5/2004 | Schneck et al. |
| 7,041,442 B1 | 5/2006 | Kern et al. |
| 7,060,869 B2 | 6/2006 | Tsien et al. |
| 7,064,190 B1 | 6/2006 | Endl et al. |
| 7,074,904 B2 | 7/2006 | Wong et al. |

(Continued)

FOREIGN PATENT DOCUMENTS

DE    197 40 735    3/1999
DE    102 47 014    4/2004

(Continued)

OTHER PUBLICATIONS

Fei et al. (Experimental Hematology 2008;36:1297-1308, published online Jul. 10, 2008).*
Cannons et al., Current Opinion in Immunology 2004, 16:296-303.*
Tsygankov, Frontiers in Bioscience 8, s595-635, May 1, 2003.*
The biology of cancer, Robert Weinberg, Garland Science, 2007, pp. 737-747.*
Lauristein et al., The Journal of Immunology, 1998, 161: 260-267.*
Kao et al., International Immunology, vol. 17, No. 12, pp. 1607-1617.*
Drake et al., The Journal of Immunology, 2001, 166: 7009-7013.*
Kronenberg et al., Nat Rev Immunol. Aug. 2002;2(8):557-68.*
Chen et al., J Leukoc Biol. Dec. 2007;82(6):1455-65.*
Kao et al., International Immunology, 2005, vol. 17, No. 12, pp. 1607-1617.*

(Continued)

*Primary Examiner* — Zachary Skelding
(74) *Attorney, Agent, or Firm* — Posternak Blankstein & Lund LLP

(57) ABSTRACT

The invention relates to a method for sorting, staining or detecting T cells of the immune system using a protein kinase inhibitor.

12 Claims, 17 Drawing Sheets

(56) References Cited

U.S. PATENT DOCUMENTS

Figure 1A:
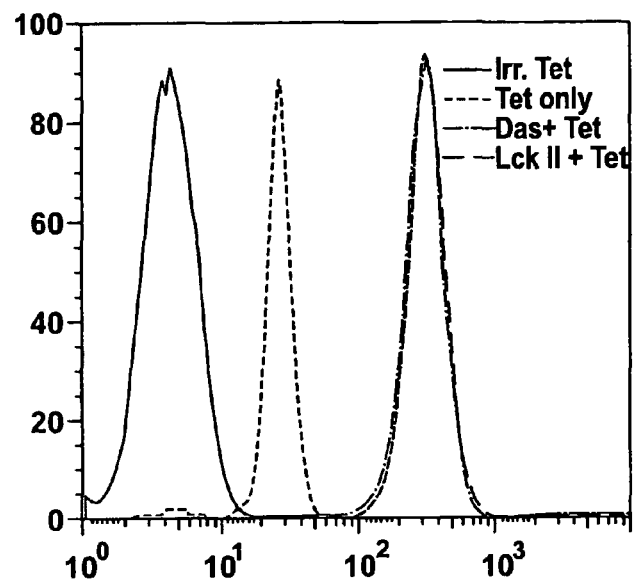

| | | | |
|---|---|---|---|
| 7,094,555 B2 | 8/2006 | Kwok et al. |
| 7,116,407 B2 | 10/2006 | Hansen et al. |
| 7,141,656 B2 | 11/2006 | Rhode et al. |
| 7,202,349 B2 | 4/2007 | Davis |
| 7,364,869 B2 | 4/2008 | Nixon et al. |
| 7,524,503 B2 | 4/2009 | Khanna et al. |
| 8,114,669 B2 | 2/2012 | Choo |
| 8,268,964 B2 | 9/2012 | Scholler et al. |
| 8,298,782 B2 | 10/2012 | Busch et al. |
| 2002/0006903 A1 | 1/2002 | Schneck et al. |
| 2002/0034513 A1 | 3/2002 | Rhode et al. |
| 2002/0058787 A1 | 5/2002 | Strominger |
| 2002/0082411 A1 | 6/2002 | Carter et al. |
| 2002/0091079 A1 | 7/2002 | Rhode et al. |
| 2002/0119149 A1 | 8/2002 | Jakobsen et al. |
| 2002/0127231 A1 | 9/2002 | Schneck |
| 2002/0164340 A1 | 11/2002 | Brumeanu et al. |
| 2002/0165364 A1 | 11/2002 | Tsien et al. |
| 2002/0198144 A1 | 12/2002 | Wong et al. |
| 2003/0017447 A1 | 1/2003 | Barnardo et al. |
| 2003/0073102 A1 | 4/2003 | Kwok et al. |
| 2003/0096432 A1 | 5/2003 | Jakobsen et al. |
| 2003/0104635 A1 | 6/2003 | Jakobsen et al. |
| 2003/0171290 A1 | 9/2003 | Carr et al. |
| 2003/0199438 A1 | 10/2003 | Shaw et al. |
| 2003/0228258 A1 | 12/2003 | Scheinberg et al. |
| 2004/0068100 A1 | 4/2004 | Mach et al. |
| 2004/0072262 A1 | 4/2004 | Montero-Julian et al. |
| 2004/0082012 A1 | 4/2004 | Busch et al. |
| 2004/0086520 A1 | 5/2004 | Diamond |
| 2004/0137642 A1 | 7/2004 | Erfle et al. |
| 2004/0141958 A1 | 7/2004 | Steinaa et al. |
| 2004/0143094 A1 | 7/2004 | Donda et al. |
| 2004/0204565 A1 | 10/2004 | Schneck et al. |
| 2004/0209295 A1 | 10/2004 | Schwabe et al. |
| 2004/0209314 A1 | 10/2004 | Lang et al. |
| 2004/0223977 A1 | 11/2004 | Diamond |
| 2004/0253632 A1 | 12/2004 | Rhode et al. |
| 2005/0003431 A1 | 1/2005 | Wucherpfennig et al. |
| 2005/0074822 A1 | 4/2005 | Nixon et al. |
| 2005/0074848 A1 | 4/2005 | Schwabe |
| 2005/0079152 A1 | 4/2005 | Bot et al. |
| 2005/0095655 A1 | 5/2005 | Montero-Julian et al. |
| 2005/0208529 A1 | 9/2005 | Winther et al. |
| 2005/0214284 A1 | 9/2005 | Price-Schiavi et al. |
| 2005/0214852 A1 | 9/2005 | Gaynor et al. |
| 2005/0239160 A1 | 10/2005 | Shaw et al. |
| 2006/0018878 A1 | 1/2006 | Cooper et al. |
| 2006/0018929 A1 | 1/2006 | Zaia et al. |
| 2006/0084116 A1 | 4/2006 | Muchhal |
| 2006/0112440 A1 | 5/2006 | Tsien et al. |
| 2006/0141540 A1 | 6/2006 | Miltenyi et al. |
| 2006/0155115 A1 | 7/2006 | Jakobsen et al. |
| 2006/0166214 A1 | 7/2006 | Kato et al. |
| 2006/0166875 A1 | 7/2006 | Jakobsen et al. |
| 2006/0171954 A1 | 8/2006 | Endl et al. |
| 2006/0228758 A1 | 10/2006 | Muchhal et al. |
| 2006/0228759 A1 | 10/2006 | Muchhal et al. |
| 2006/0234309 A1 | 10/2006 | Shankar et al. |
| 2006/0234310 A1 | 10/2006 | Cai et al. |
| 2006/0240482 A1 | 10/2006 | Kwok et al. |
| 2007/0026503 A1 | 2/2007 | Lacey |
| 2007/0134814 A1 | 6/2007 | Kajander et al. |
| 2007/0154953 A1 | 7/2007 | Brunner et al. |
| 2007/0178532 A1 | 8/2007 | Jacobson et al. |
| 2007/0280957 A1 | 12/2007 | Falk et al. |
| 2008/0219947 A1 | 9/2008 | Linette et al. |
| 2009/0004213 A1 | 1/2009 | Singh et al. |
| 2009/0061478 A1 | 3/2009 | Poulsen et al. |
| 2009/0324630 A1 | 12/2009 | Jensen |
| 2010/0159594 A1 | 6/2010 | Hansen et al. |
| 2012/0020998 A1 | 1/2012 | Plumas et al. |

FOREIGN PATENT DOCUMENTS

| | | |
|---|---|---|
| EP | 0 106 873 | 5/1984 |
| EP | 0 352 761 | 1/1990 |
| EP | 0 516 953 | 12/1992 |
| EP | 0 633 028 | 1/1995 |
| EP | 0 636 696 | 2/1995 |
| EP | 0 665 289 | 2/1995 |
| EP | 0 420 913 | 11/1995 |
| EP | 0 423 201 | 6/1996 |
| EP | 0 742 014 | 11/1996 |
| EP | 0 949 508 | 10/1999 |
| EP | 0946592 | 10/1999 |
| EP | 1023319 | 8/2000 |
| EP | 0 776 339 | 10/2000 |
| EP | 1 051 619 | 11/2000 |
| EP | 1181313 | 2/2002 |
| EP | 0 981 747 | 7/2002 |
| EP | 1 227 321 | 7/2002 |
| EP | 0 630 255 | 12/2002 |
| EP | 0 812 331 | 5/2004 |
| EP | 0 935 607 | 7/2004 |
| EP | 1 437 366 | 7/2004 |
| EP | 0 877 760 | 9/2004 |
| EP | 1 526 141 | 8/2005 |
| EP | 0 997 477 | 3/2006 |
| EP | 1 017 799 | 3/2006 |
| EP | 1 349 569 | 4/2007 |
| EP | 1 012 320 | 10/2007 |
| RU | 2 260 047 | 4/2005 |
| WO | WO 89/12458 | 12/1989 |
| WO | WO 89/12459 | 12/1989 |
| WO | WO 90/04411 | 5/1990 |
| WO | WO 91/09870 | 7/1991 |
| WO | WO 91/15766 | 10/1991 |
| WO | WO 92/00055 | 1/1992 |
| WO | WO 92/08983 | 5/1992 |
| WO | WO 92/18150 | 10/1992 |
| WO | WO 92/21972 | 12/1992 |
| WO | WO 93/01498 | 1/1993 |
| WO | WO 93/04175 | 3/1993 |
| WO | WO 93/08306 | 4/1993 |
| WO | WO 93/10220 | 5/1993 |
| WO | WO 94/11078 | 5/1994 |
| WO | WO 94/12196 | 6/1994 |
| WO | WO 95/11998 | 5/1995 |
| WO | WO 95/12676 | 5/1995 |
| WO | WO 95/14781 | 6/1995 |
| WO | WO 96/04314 | 2/1996 |
| WO | WO 96/26962 | 9/1996 |
| WO | WO 97/05239 | 2/1997 |
| WO | WO 97/28191 | 8/1997 |
| WO | WO 97/35991 | 10/1997 |
| WO | WO 97/42221 | 11/1997 |
| WO | WO 97/44667 | 11/1997 |
| WO | WO 98/03552 | 1/1998 |
| WO | WO 98/05965 | 2/1998 |
| WO | WO 98/06749 | 2/1998 |
| WO | WO 98/05684 | 12/1998 |
| WO | WO 99/02183 | 1/1999 |
| WO | WO 99/11661 | 3/1999 |
| WO | WO 99/11775 | 3/1999 |
| WO | WO 99/14236 | 3/1999 |
| WO | WO 99/21572 | 5/1999 |
| WO | WO 99/13095 | 7/1999 |
| WO | WO 99/36568 | 7/1999 |
| WO | WO 99/42597 | 8/1999 |
| WO | WO 99/50637 | 10/1999 |
| WO | WO 99/58557 | 11/1999 |
| WO | WO 99/60119 | 11/1999 |
| WO | WO 00/06745 | 2/2000 |
| WO | WO 00/15665 | 3/2000 |
| WO | WO 00/23053 | 4/2000 |
| WO | WO 00/75180 | 12/2000 |
| WO | WO 00/78966 | 12/2000 |
| WO | WO 03/000720 | 1/2001 |
| WO | WO 01/63286 | 8/2001 |
| WO | WO 01/72782 | 10/2001 |
| WO | WO 01/70245 | 11/2001 |

(56) References Cited

FOREIGN PATENT DOCUMENTS

| WO | WO 01/80833 | 11/2001 |
|---|---|---|
| WO | WO 01/90198 | 11/2001 |
| WO | WO 01/90747 | 11/2001 |
| WO | WO 02/16422 | 2/2002 |
| WO | WO 02/054065 | 7/2002 |
| WO | WO 02/055992 | 7/2002 |
| WO | WO 02/072631 | 9/2002 |
| WO | WO 02/083906 | 10/2002 |
| WO | WO 02/089837 | 11/2002 |
| WO | WO 03/016905 | 2/2003 |
| WO | WO 03/073097 | 9/2003 |
| WO | WO 03/101473 | 12/2003 |
| WO | WO 2004/000873 | 12/2003 |
| WO | WO 2004/014957 | 2/2004 |
| WO | WO 2004/018520 | 3/2004 |
| WO | WO 2004/033497 | 4/2004 |
| WO | WO 2004/093905 | 11/2004 |
| WO | WO 2005/002621 | 1/2005 |
| WO | WO 2005/007689 | 1/2005 |
| WO | WO 2005/035567 | 4/2005 |
| WO | WO 2005/049073 | 6/2005 |
| WO | WO 2005/116051 | 12/2005 |
| WO | WO 2006/009838 | 1/2006 |
| WO | WO 2006/014292 | 2/2006 |
| WO | WO 2006/056027 | 6/2006 |
| WO | WO 2006/071990 | 7/2006 |
| WO | WO 2006/081826 | 8/2006 |
| WO | WO 2006/082387 | 8/2006 |
| WO | WO 2006/090283 | 8/2006 |
| WO | WO 2006/113622 | 10/2006 |
| WO | WO 2007/065098 | 6/2007 |
| WO | WO 2007/085266 | 8/2007 |
| WO | WO 2007/136778 | 11/2007 |
| WO | WO 2008/019366 | 2/2008 |
| WO | WO 2008/031133 | 3/2008 |
| WO | WO 2008/116468 | 10/2008 |
| WO | WO 2009/003492 | 1/2009 |
| WO | WO 2009/003493 | 1/2009 |
| WO | WO 2009/039854 | 4/2009 |
| WO | WO 2009/106073 | 9/2009 |
| WO | WO 2009/114207 | 9/2009 |
| WO | WO 2009/125231 | 10/2009 |
| WO | WO 2009/126816 | 10/2009 |
| WO | WO 2009/155535 | 11/2009 |
| WO | WO 2010/009735 | 1/2010 |
| WO | WO 2010/037395 | 4/2010 |
| WO | WO 2010/037397 | 4/2010 |
| WO | WO 2010/037402 | 4/2010 |

OTHER PUBLICATIONS

U.S. Appl. No. 08/374,468, Not published, Endl.

Alp, et al., "Fine specificity of cellular immune responses in humans to human cytomegalovirus immediate-early 1 protein", Journal of Virology, vol. 65, No. 9, 1991 pp. 4812-4820.

Altman,, et al., "Formation of functional peptide complexes of class II major histocompatibility complex proteins from subunits produced in Escherichia coli," Proc. Natl. Acad. Sci. USA, pp. 10330-10334, Nov. 1993, vol. 90.

Altman,, et al., "Phenotypic Analysis of Antigen-Specific T Lymphocytes," Science 274:94-97, 1996.

Andersen,, et al., "Spontaneous cytotoxic T-cell responses against survivin MHC class I-restricted T-cell epitopes in situ as well as ex vivo in cancer patients," Cancer Res., vol. 61, pp. 5964-5968, Aug. 15, 2001.

Appel,, et al., "Kinetics of T-cell receptor binding by bivalent HLA-DR-peptide complexes that activate antigen-specific human T-cells," J. Biol. Chem., pp. 312-321, Jan. 7, 2000, vol. 275.

Appel,, et al., "Anergy induction by dimeric TCR ligands," J. Immunol., pp. 5279-5285, Apr. 15, 2001, vol. 166.

Ausubel,, et al., "Characterization of in vivo expanded OspA-specific human T-cell clones," Clinical Immunology, Academic Press, pp. 313-322, Jun. 1, 2005, vol. 115, No. 3, US.

Bakker,, et al., "MHC multimer technology: Current status and future prospects," Current Opinion in Immunology, 17:428-433, 2005.

Barany,, et al., "Solid-phase peptide synthesis: A silver anniversary report," Int. J. Peptide Protein Res., 30:705-739, 1987.

Batard,, et al., "Dextramers: New generation of fluorescent MHC class I/ peptide multimers for visualization of antigen-specific CD8<+> T cells," Journal of Immunological Methods, Elsevier Science Publishers, pp. 136-148, Mar. 20, 2006, vol. 310, No. 1-2, Amsterdamn, NL.

Berger,, et al., "Circulation and homing of melanoma-reactive T cells to both cutaneous and visceral metastases after vaccinnation with monocyte-derived dendritic cells," Int. J. Cancer, pp. 229-237, 2004, vol. 111.

Bergmeier,, et al., "Innate and adoptive mucosal immunity in protection against HIV infection," Advances in Dental Research 2006, pp. 21-28, 2006, vol. 19, No. 1, XP002562924.

Bill,, et al., "Use of soluble MHC class II/peptide multimers to detect antigen-specific T cells in human disease," Arthritis Res., pp. 261-265, Feb. 28, 2002, vol. 4.

Bjorkman,, et al., "The foreign antigen binding site and T cell recognition regions of class I histocompatibility antigens," Nature 329:512-518, 1987.

Bleesing, et al., "Cell Function-Based Flow Cytometry" Seminars in Hematology, Apr. 2001, pp. 169-178, vol. 38, No. 2.

Bogers, "CCR5 targeted SIV vaccination strategy preventing or inhabiting SIV infection," Vaccine, Butterworth Scientific, pp. 2974-2984, Aug. 13, 2004, vol. 22, No. 23-24. Guildford, GB.

Bross, et al., "Approval summary: Gemtuzumab ozogamicin in relapsed acute myeloid leukemia", Clin. Cancer Res., 2001, 7:1490-1496.

Burlingham et al., "Soluble MHC, Immunoregulation, and tolerance: A progress report," Human Immunol., pp. 1316-1319, Dec. 2000, vol. 61.

Callan,, et al., "Direct Visualization of Antigen.specific CD8+ T Cells during the Primary Immune Response to Epstein-Barr Virus in Vivo," J. Exp. Med., May 1998, pp. 1395-1402, vol. 187, No. 9.

Cameron, et al., "Labeling antigen-specific DC4(+) T cells with class II MHC oligomers," J. Immunol. Methods, pp. 51-69, Oct. 1, 2002, vol. 268.

Carena, et al., "Major Histocompatibility Complex Class I Molecules Modulate Activation Threshold and Early Signaling of T-Cell Antigen Receptor-$\gamma\delta$ Stimulated by Nonpeptidic Ligands," J. Exp. Med., Nov. 17, 1997, pp. 1769-1774, 186 (10).

Casares, et al., "Antigen-specific downregulation of T cells by doxorubicin delivered through a recombinant MHC II-peptide chimera," Nature Biotech., pp. 142-147, Feb. 2001, vol. 19.

Cecconi, et al., "Use of MHC Class II Tetramers to Investigate CD4 + T Cell Responses: Problems and Solutions," Cytrometry, 2008, Part A 73, No. 11, pp. 1010-1018.

Chattopadhyay, et al.,"Techniques to improve the direct Ex Vivo detection of low frequency antigen-specific CD8+T cells with peptide-major histocompatibility complex class I tetramers," Cytometry, 2008, Part A, vol. 73, pp. 1001-1009.

Cochran, et al., "Receptor clustering and transmembrane signaling T cells," TIBS, pp. 304-310, May 2001, vol. 26.

Coles, et al., "Memory CD8 T lymphocytes express inhibitory MHC-specific Ly49 receptors," EUR. J. Immunol. 30:236-244, 2000.

Constantin, et al., "Major histocompatibility complex (MHC) tetramer technology: An evaluation," Biol. Res. Nursing, pp. 115-127, Oct. 2002, vol. 4.

Dako: "MHC Dextramers" Internet Article Jul. 6, 2006 URL: pri.dako.com/00207_mhcdex_0406.pdf.

Dal Porto et al, "A soluble divalent class I major histocompatibility complex molecule inhibits alloreactive T cells at nanomolar concentrations," Porc. Natl. Acad. Sci. 90.6671-6675, 1993.

Devito-Haynes, et al., "Soluble donor HLA class I and $\beta_2$-m-free heavy chain in serum of lung transplant recipients: Steady-state levels and increases in patients with recurrent CMV infection, acute rejection episodes, and poor outcome," Human Immunol., pp. 1370-1382, Dec. 2000, vol. 61.

Drouin, et al., "Molecular Characterization of the $OspA_{161-175}$ T cell epitope associated with the treatment-resistant Lyme Arthritis: dif-

(56) References Cited

OTHER PUBLICATIONS ferences among the three pathogenic species of *Borrelia burgdorferi* sensu lato", Journal of Autoimmunity, 2004, vol. 23, No. 3, pp. 281-292.

Drouin et al., "Searching for borrelial T-cell epitopes associated with antibiotic-refractory Lyme arthritis," Molecular Immunology, pp. 2323-2332, Jan. 11, 2008, vol. 45, No. 8, GB.

Ed. Charron, "HLA: Genetic diversity of HLA. Functional and Medical Implication," EDK Press, pages corresponding to Tables 1A and 1B, 1997.

Erout, et al., "Preparation of Conjugates between Oligonucleotides and N-Vinylpyrrolidone/N-Acryloxysuccinimide Coplymers and Applications in Nucleic Acid Assays to Improve Sensitivity," Bioconjugate Chem. 1996, pp. 568-575, vol. 7.

Fields, et al., "Solid phase peptide synthesis utilizing 9-fluorenylmethoxycarbonyl amino acids," Int. J. Peptide Res., 353:161-214, 1990.

Fornas, et al., Flow Cytometry Counting of CD34+ cells in whole blood, Nature Medicine, 6 (2000) 7:833-836.

Frayser, et al., "Empty and peptide-loaded class II major histocompatibility complex proteins produced by expression in *Escherichia coli* and folding in vitro," Protein Expression and Purification, pp. 105-114, Feb. 1999, vol. 15.

Garboczi, et al., "HLA-A2.peptide complexes: Refolding and crystallization of molecules expressed in *Escherichia coli* and complexed with single antigenic peptides," Proc. Natl. Acad. Sci., 89:3429-3433, 1992.

Gordon, et al., "Applications of Combinatorial Technologies to Drug Discovery. 2. Combinatorial Organic Synthesis, Library Screening Strategies, and Future Directions," Journal of Medicinal Chemistry, 37 (10):1385-1401, 1994.

Hadrup, et al., "Persistence of survivin specific T cells for seven years in a melanoma patient during complete remission," Cancer Biol. & Ther., pp. 480-482, May, 2006, vol. 5.

Heijnen, et al., " Enumeration of Antigen-Specific CD8+ T Lymphocytes by Single-Platform, HLA Tetramer-Based Flow Cytometry: A European Multicenter Evaluation", Clinical Cytometry, 2004, pp. 1-13, vol. 62B.

Houghten, et al., "Generation and use of synthetic peptide combinatorial libraries for basic research and drug discovery," Nature, 354:84-86, 1991.

Hugues, et al., "Generation and use of alternative multimers of peptide/MHC complexes," Journal of Immunological Methods, 268:83-92, 2002.

Haanen, et al., "In situ detection of virus- and tumor-specific T-cell Immunity," Nature Medicine, Sep. 2000, pp. 1056-1060, vol. 6.

International Search report mailed May 6, 2007 in International Application No. PCT/DK2007/000045 (=P151PC00).

Jung, et al., "Multiple Peptide Synthesis Methods and their Applications," Angewandte Chemie, 31 (4):367-486, 1992.

Kalandadze, et al., "Expression of Recombinant HLA-DR2 molecules," J. Biol. Chem., pp. 20156-20162, Aug. 16, 1996, vol. 271.

Knabel, et al., "Reversible MHC multimer staining for functional isolation of T-cell populations and effective adoptive transfer," Nature Medicine, Nature Publishing Group, pp. 631-637, Jun. 1, 2002, vol. 8, No. 6, New York, NY, USA.

Kozono, et al., "Production of soluble MHC class II proteins with covalently bound single peptides," Nature, pp. 151-154, May 12, 1994, vol. 369.

Kuroda, et al., "Analysis of Gag-specific Cytotoxic T Lymphocytes in Simian Immunodeficiency Virus-intected Rhesus Monkeys by Cell Staining with Tetrameric Major Histocompatibility Complex Class I-Peptide Complex," J.Exp. Med., May 4, 1998, 1373-1381, vol. 187, No. 9.

Kuttler, et al., "An Algorithm for the Prediction of Proteasomal Cleavages," J. Mol. Biol., 298:417-429, 2000.

König, "Interactions between MHC molecules and co-receptors of the TCR," Current Opinion in Immunology, pp. 75-83, 2002, vol. 14.

Larsson, "Immunocytochemical detection systems," in Immunocytochemistry: Theory and Practice, pp. 77-145, CRC Press, 1988.

Lee, et al., "Characterization of circulating T cells specific for tumor-associated antigens in melanoma patients," Nature Medicine, Jun. 1999, pp. 677-685, vol. 5, No. 6.

Lehner, "Allomicrovac: A combined microbicidal-immunising strategy against SIV and HIV infection,"Vaccines for Humans, pp. 64-65, Dec. 5, 2008, XP0025629223, URL: http://www.biblioteca.porto.ucp.pt/docbweb/MULTIMEDIA/ASSOCIA/PDF/VAC.PDF.

Lissina, et al.,"Protein Kinase Inhibitors Substantially Improve the Physical Detection of T-Cells with Peptide-MHC Tetramers," J. Immunol. Methods, 2009, vol. 340, pp. 11-24.

Ljunggren, et al., "Empty MHC class I molecules come out in the cold," Nature 346:476-480, 1990.

Mallone, et al., "MHC class II tetramers and the pursuit of antigen-specific T cells: Define, deviate, delete," Clin. Immunol., pp. 232-242, 2004, vol. 110.

Maloney, et al., "IDEC-C2B8 (Rituximab) anti-CD20 monoclonal antibody therapy in patients with relapsed low-grade non-Hodgkin's lymphoma," Sep. 1997, Blood, 90 (6):2188-2195.

Marchand, et al., "Tumor regression responses in melanoma patients treated with a peptide encoded by gene MAGE-3,"Int. J. Cancer, 63:883-885, 1995.

Marsh, et al., "12th International Histocompatibility Workshop Cell Lines Panel: List of Cell Lines", Genetic diversity of HLA Functional and Medical Implication, (Charron ed.), pp. 26-28, 1997.

Matsumura, et al., "Emerging Principles for the Recognition of Peptide Antigens by MHC class I Molecules," Science 257:927-934, 1992.

Matsumura, et al., "In vitro peptide binding to soluble empty calss I major histocompatibility complex molecules isolated from transfected Drosophila melanogaster cells," J. Biol. Chem., pp. 23589-23595, Nov. 25, 1992, vol. 267.

McCluskey, et al., "T-cell activation by purified, soluble , class I MHC molecules: Requirement for polyvalency," J. Immunol. 141(5): 1451-55, 1988.

McHeyzer-Williams, et al., "Tracking antigen-specific helper T cell responses," Current Opinion in Immunology, pp. 278-284, 1996, vol. 8.

Melenhorst, et al.,"Detection of Low Avidity CD8+ T Cell Populations with Coreceptor-Enhanced Peptide-Major Histocompatibility Complex Class I Tetramers," J. Immunol. Methods, 2008, vol. 338, No. 1-2, pp. 31-39.

Merrifield, "Solid Phase Synthesis," Science 232:341-347, 1986.

Merrifield, et al., "Instrument for Automated Synthesis of peptides," Analytical Chemistry, 38 (13):1905-1914, 1966.

Meyer, et al., "Direct enumeration of Borrelia-reactive CD4 T-cell ex vivo by using MHC class II tetramers," Proceedings of the National Academy of Sciences of USA. (PNAS), National Academy of Science, pp. 11433-11438, Oct. 10, 2000, vol. 97, No. 21, Washington D.C., US.

Mutis, et al., "Tetrameric HLA class I-minor histocompatability antigen peptide complexes demonstrate minor histocompatibility antigen-specific cytoxic T lymphocytes in patients with graft-visus-host disease," Nature Medicine, Jul. 1999, pp. 839-842, vol. 5, No. 7.

Neudorfer, et al., "Reversible HLA multimers (streptamers) for the isolation of human cytotoxic T lymphocytes functionally active against tumor- and virus-derived antigens," Journal of Immunological Methods, 320:119-131, 2007.

O'Herrin, et al., "Analysis of the Expression of Peptide-Major Histocompatibility Complexes using high affinity Soluble Divalent T-Cell Receptors," J. Exp. Med., Oct. 20, 1997, pp. 1333-1345, vol. 186, No. 8.

Reich, et al., "Stability of empty and peptide-loaded class II major histocompatibility complex molecules at neutral and endosomal pH: Comparison to class I proteins," Proc. Natl. Acad. Sci. USA, pp. 2495-2500, Mar. 1997, vol. 94.

Reijonen, et al., "Use of HLA class II tetramers in tracking antigen-specific T cells and mapping T-cell epitopes," Science Direct, Methods vol. 29, pp. 282-288, 2003.

Scheffold, et al., "Recent Development in Flow Cytometry," Journal of Clinical Immunology, pp. 400-407, Aug. 2000, vol. 20, No. 6.

(56) References Cited

OTHER PUBLICATIONS

Scheirle, et al., "Peptide binding to soluble HLA-DR4 molecules produced by insect cells," J. Immunol., pp. 1994-1999, Sep. 15, 1992, vol. 149.

Sengupta, et al., "Heat shock protein-mediated cross-presentation of exogenous HIV antigen on HLA class I and class II," Journal of Immunology, American Association of Immunologists, pp. 1987-1993, Aug. 1, 2004, vol. 173, No. 3.

Shambrook, Fritsch and Maniatis, "Molecular Cloning," Cold Spring Harbor Press, 1989, Index and Table of Contents pp. xi to xxxviii and I-1 to I-47.

Shields, et al., "The Effect of Human $\beta_2$- Microglobulin on Major Histocompatibility Complex I Peptide Loading and the Engineering of a High Affinity Variant," The Journal of Biological Chemistry, Oct. 23, 1998, pp. 28010-28018, vol. 273, No. 43.

Siiman, et al., "Fluorescent Neoglycoproteins: Antibody-Aminodextran-Phycobiliprotein Conjugates," Bioconjugate Chem. 1999, vol. 10, pp. 1090-1106.

Skinner, et al., "In situ tetramer staining," J. Immunol. Meth., pp. 29-34, 2002, vol. 268.

Stern, et al., "The human class II MHC protein HLA-DR1 assembles as empty alpha beta heterodimers in the absence of antigenic peptide," Cell, pp. 465-477, Feb. 7, 1992, vol. 68.

Stratmann, et al., "Susceptible MHC Alleles, not background genes, select an autoimmune T cell reactivity," The Journal of Clinical Investigation, pp. 902-914, Sep. 2003, vol. 112, No. 6.

Stöckel, et al., "Refolding of human class II major histocompatibility complex molecules isolated from *Escherichia coli*", J. Biol. Chem., pp. 29571-29578, Nov. 25, 1994, vol. 269.

Sun, et al., "MHC class I multimers," Arthritis Res., pp. 265-269, Jul. 2001, vol. 3.

Sørensen, et al., "Efficient tumor cell lysis mediated by a Bcl-X(L) specific T cell clone isolated from a breast cancer patient," Cancer Immunol., Immunotherapy, Springer, pp. 527-533, Jul. 19, 2006, vol. 56, No. 4, Berlin, DE.

Ugolini, et al., "Regulation of T cell function by NK cell receptors for classical MHC class I molecules," Current Opinion in Immunology 12:295-300, 2000.

Valmori, et al., "Enhanced generation of specific tumor-reactive CTL in vitro by selected Melan-A/MART-1 immunodominant peptide analogues," J. Immunol., pp. 1750-1758, Feb. 15, 1998, vol. 160.

Viola, et al., "T-cell activation and the dynamic world of rafts.," APMIS 107:615-623, 1999.

Vollers, et al.,"Class II Major Histocompatibility Complex Tetramer Staining: Progress, Problems, and Prospects," Immunology, 2008, vol. 123, pp. 305-313.

Vyth-Dreese, et al., "In situ visualization of antigen specific T cells in cryopreserved human tissues," J. Immunol. Meth., pp. 78-85, 2006, vol. 310.

Weichsel, et al.,"Profound Inhibition of Antigen-Specific T-Cell Effector Functions by Dasatinib," Clin. Cancer Res. 2008, vol. 14, pp. 2484-2491.

White, et al., "Soluble class I MHC with β2-microglobulin covalently linked peptides: Specific binding to a T cell hybridoma," J. Immunol., pp. 2671-2676, Mar. 1, 1999, vol. 162.

Wolfl, et al., "Quantitation of MHC Tetramer-Positive Cells From Whole Blood: Evaluation of Single-Platform, Six-parameter Flow Cytometric Method", Cytometry Part A, 2004, pp. 120-130, vol. 57A.

Xu, et al., "MHC/peptide tetramer-based studies of T cell function," J. Immunol Meth., pp. 21-28, 2002, vol. 268.

Zhang, et al., "Essential role of LAT in T cell development," Immunity 10:323-332, 1999.

Batard et al., "Dextramers: New Generation of Fluorescent MHC Class I/Peptide Multimers for Visualization of Antigen-Specific CD8+ T cells," J. Immunol. Methods 310:136-148, 2006.

Cecconi et al., "Use of MHC Class II Tetramers to Investigate CD4+ T Cell Response: Problems and Solutions," Cytometry Part A 73:1010-1018, 2008.

Chattopadhyay et al., "Techniques to Improve the Direct Ex Vivo Detection of Low Frequency Antigen-Specific CD8+ T Cells with Peptide-Major Histocompatibility Complex Class I Tetramers," Cytometry Part A 73:1001-1009, 2008.

Lissina et al., "Protein Kinase Inhibitors Substantially Improve the Physical Detection of T-Cells with Peptide-MHC Tetramers," J. Immunol. Methods 340:11-24, 2009.

Melenhorst et al., "Detection of Low Avidity CD8+ T Cell Populations with Coreceptor-Enhanced Peptide-Major Histocompatibility Complex Class I Tetramers," J. Immunol. Methods 338:31-39, 2008.

Vollers and Stern, "Class II Major Histocompatibility Complex Tetramer Staining: Progress, Problems, and Prospects," Immunology 123:305-313, 2008.

Weichsel et al., "Profound Inhibition of Antigen-Specific T-Cell Effector Functions by Dasatinib," Clin. Cancer Res. 14:2484-2491, 2008.

Ferré, et al., "Purification of correctly oxidized MHC class I heavy-chain molecules under denaturing conditions: A novel strategy exploiting disulfide assisted protein folding", Protein Science, 2003, 12, pp. 551-559.

Akiyama, "Analysis of HLA-A24-restricted CMVpp65 peptide-specific CTL with HLA-A*2402-CMVpp65 tetramer," Immunology Letters, vol. 95, Issue 2, pp. 199-205 (2004).

Celis, "Identification of potential CTL Epitopes of Tumor-Associated Antigen Mage-1 for Five Common HLA-A Alleles," Molecular Immunology, vol. 31, No. 18, pp. 1423-1430 (1994).

Denkberg, "Recombinant human single-chain MHC-peptide complexes made from *E. coli* by in vitro refolding: functional single-chain MHC-peptide complexes and tetramers with tumor associated antigens," Eur. J. Immunol., vol. 30, pp. 3522-3532 (2000).

Dibrino, "Endogenous peptides bound to HLA-A3 possess a specific combination of anchor residues that permit identification of potential antigenic peptides," Proc. Natl. Acad. Sci. USA, vol. 90, pp. 1508-1512 (1993).

He, "Procedure for preparing peptide-major histocompatibility complex tetramers for direct quantification of antigen-specific cytotoxic T lymphocytes," World J Gastroenterol, vol. 11, No. 27, pp. 4180-4187 (2005).

IEBD Analysis Resource, at; tools.immuneepitiope.org/tools/population/tutorial.jsp (3 pages).

Karin, "Reversal of Experimental Autoimmune Encephalomyelitis by a Soluble Peptide Variant of a Myelin Basic Protein Epitope: T Cell Receptor Antagonism and Reduction of Interferon γ and Tumor Necrosis Factor α Production," J. Exp. Med., vol. 180, pp. 2227-2237 (1994).

Nepom, "MHC Multimers: expanding the clinical toolkit," Clinical Immunology, vol. 106, pp. 1-4 (2003).

Parker, "Peptide Binding to HLA-A2 and HLA-B27 Isolated from *Escherichia coli*," The Journal of Biological Chemistry, vol. 267, pp. 5451-5459 (1992).

Rognan, "Rational design of nonnatural peptides as high-affinity ligands for the HLA-B*2705 human leukocyte antigen," Proc. Natl. Acad. Sci. USA, vol. 92, pp. 753-757 (1995).

Ruan, "Preparation of HLA-A*0201 NLVPMVATV peptide tetramers and application to detect cytomegalovirus specific CTL," Zhonghua Weishengwuxue He Mianyixue Zazhi, vol. 26., No. 9, pp. 855-858 (2006)—English Abstract Only.

Ruan, "Improved preparation of class I HLA tetramers and their use in detecting CMV-specific CTL," Journal of Immunological Methods, vol. 312, pp. 148-156 (2006).

Wulff, "Guide to Flow Cytometry," Dako Educational Guide, www.dako.com, (2006).

* cited by examiner

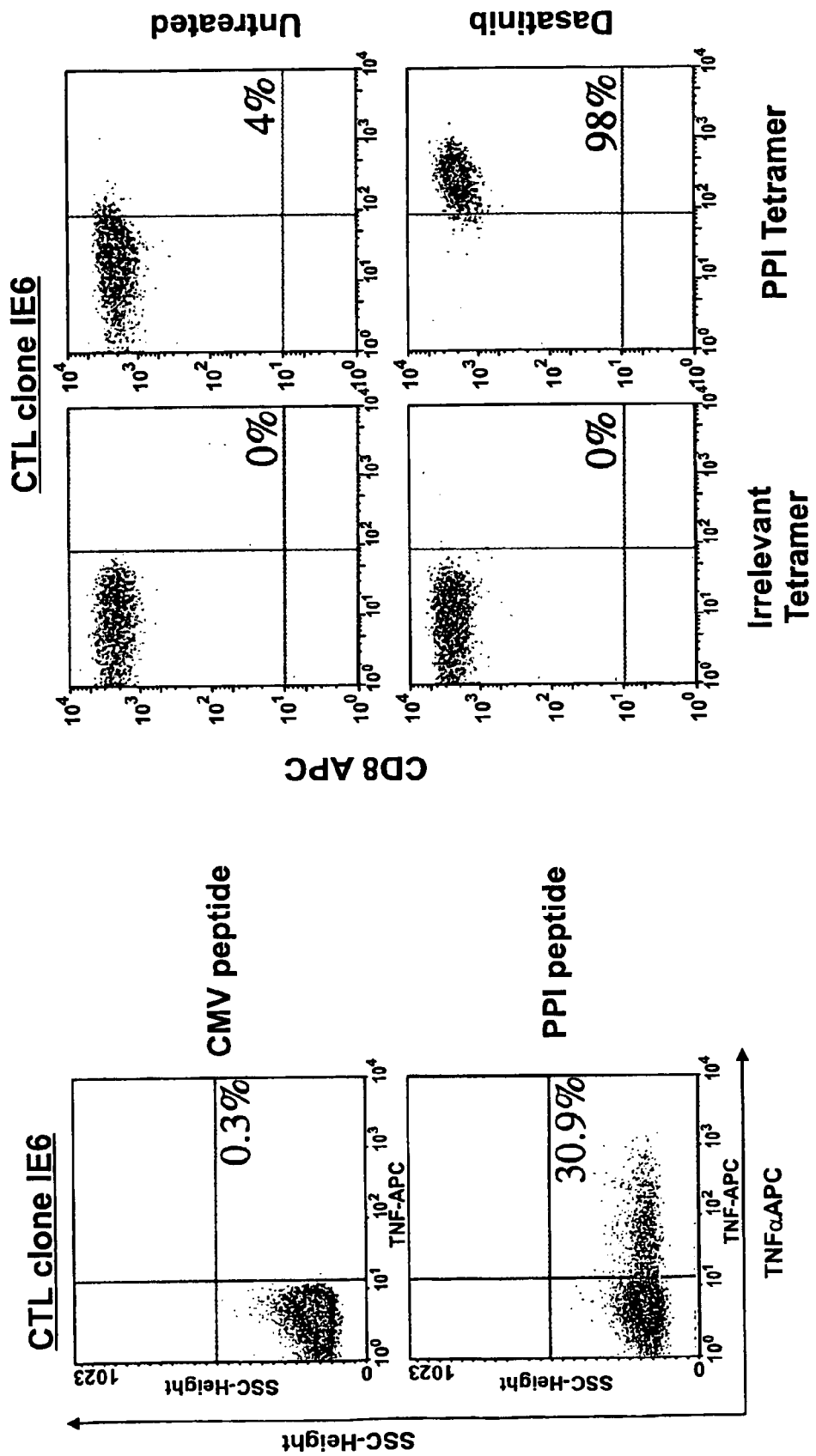

SEQUENCE LISTING

```
<160> NUMBER OF SEQ ID NOS: 8

<210> SEQ ID NO 1
<211> LENGTH: 9
<212> TYPE: PRT
<213> ORGANISM: Homo sapiens

<400> SEQUENCE: 1

Ile Leu Ala Lys Phe Leu His Trp Leu
1               5

<210> SEQ ID NO 2
<211> LENGTH: 10
<212> TYPE: PRT
<213> ORGANISM: Homo sapiens

<400> SEQUENCE: 2

Glu Leu Ala Gly Ile Gly Ile Leu Thr Val
1               5                   10
```

```
<210> SEQ ID NO 3
<211> LENGTH: 9
<212> TYPE: PRT
<213> ORGANISM: Cytomegalovirus

<400> SEQUENCE: 3

Asn Leu Val Pro Met Val Ala Thr Val
1               5

<210> SEQ ID NO 4
<211> LENGTH: 9
<212> TYPE: PRT
<213> ORGANISM: Herpesvirus 4

<400> SEQUENCE: 4

Gly Leu Cys Thr Leu Val Ala Met Leu
1               5

<210> SEQ ID NO 5
<211> LENGTH: 9
<212> TYPE: PRT
<213> ORGANISM: Influenza A virus

<400> SEQUENCE: 5

Gly Ile Leu Gly Phe Val Phe Thr Leu
1               5

<210> SEQ ID NO 6
<211> LENGTH: 10
<212> TYPE: PRT
<213> ORGANISM: Homo sapiens

<400> SEQUENCE: 6

Ala Leu Trp Gly Pro Asp Pro Ala Ala Ala
1               5                   10

<210> SEQ ID NO 7
<211> LENGTH: 9
<212> TYPE: PRT
<213> ORGANISM: Influenza A virus

<400> SEQUENCE: 7

Ala Ser Asn Glu Asn Met Asp Ala Met
1               5

<210> SEQ ID NO 8
<211> LENGTH: 13
<212> TYPE: PRT
<213> ORGANISM: Influenza A virus

<400> SEQUENCE: 8

Pro Lys Tyr Val Lys Gln Asn Thr Leu Lys Leu Ala Thr
1               5                   10
```

USE OF A PROTEIN KINASE INHIBITOR TO DETECT IMMUNE CELLS, SUCH AS T CELLS

CROSS REFERENCE TO RELATED APPLICATIONS

This is the U.S. National Stage of International Application No. PCT/GB2009/002251, filed Sep. 18, 2009, which was published in English under PCT Article 21(2), which in turn claims the benefit of Great Britain Application No. 0817244.7, filed Sep. 20, 2008.

The invention relates to the use of a protein kinase inhibitor to detect cells of the immune system and in particular T cells; and also to a method for the detection of cells of the immune system, and in particular T cells, comprising the use of a protein kinase inhibitor; a method for conserving reagents when detecting cells of the immune system, and in particular T cells, comprising the use of a protein kinase inhibitor; the use of a protein kinase inhibitor in cell sorting of immune cells and in particular T cells; and also a method of cell sorting immune cells and in particular T cells comprising the use of a protein kinase inhibitor.

INTRODUCTION

T-cells detect antigens in the form of peptides bound to major histocompatibility complex (MHC) molecules at the cell surface. This primary recognition event enables the orchestration of adaptive immunity and targeted destruction of transformed and pathogen-infected cells. T-cell specificity is determined by the highly variable complementarity determining regions of the T cell receptor (TCR). The TCR/peptide-MHC (pMHC) interaction is very weak and classically endures for no longer than a few seconds at physiological temperatures. However, multimerization of pMHC molecules results in cooperative interactivity at the cell surface and ensures that the binding avidity of pMHC tetramers far exceeds the sum of the contributing monomeric affinities. This avidity effect extends the binding half-life, of pMHC tetramers (Laugel et al., 2005) and enables stable coherence to the surface of T-cells bearing cognate TCRs (Altman et al., 1996; Burrows et al., 2000). Consequently, pMHC tetramers have transformed the study of antigen-specific T-cells by enabling their visualization, enumeration, phenotypic characterization and isolation from ex vivo samples (Altman et al., 1996; Chattopadhyay et al., 2006). Indeed, pMHC tetramers have been used in thousands of studies in the decade since their initial inception and have spawned the formation of several commercial companies.

We have recently used a monoclonal T-cell system to examine T-cell activation and pMHC class I (pMHCI) tetramer binding with a series of altered peptide ligands that vary in their affinity for the cognate TCR by over 100-fold (Laugel et al., 2007). Importantly, cell surface topography, including TCR and CD8 density, remain constant in this system. In this controlled system, efficient staining with tetrameric pMHCI required a monomeric TCR/pMHCI affinity of $K_D < 35$ μM; below this threshold, there was a sharp drop off in the intensity of pMHCI tetramer staining (Laugel et al., 2007). A reasonable T-cell agonist in this system bound with a $K_D \sim 250$ μM and a weak agonist bound with a $K_D > 500$ μM. However, TCR/pMHCI affinities of >200 μM were not detectable by pMHCI tetramer. Thus, using normal staining procedures, pMHC tetramers do not necessarily detect all T-cells that can respond to a particular agonist; similarly, not all agonists for a particular T-cell can be identified physically with pMHC tetramers. These potential limitations of pMHC tetramer staining, which likely extend across a range of multimeric valencies, have important implications for data interpretation and present a particular problem for the detection of tumour-specific or autoreactive T-cells that tend to express low affinity TCRs (Cole et al., 2007).

In this study, we demonstrate that pre-treatment with a protein kinase inhibitor (PKI) enhances multimerized MHC staining and in particular pMHC tetramer staining of antigen-specific $CD8^+$ and $CD4^+$ T-cells and describe the mechanism through which these effects operate.

Protein kinases are enzymes that modify other proteins by chemically adding phosphate groups to them (phosphorylation). This involves the removal of a phosphate group from ATP and covalently attaching it to one of three-amino acids that have a free hydroxyl group. Most kinases act on both serine and threonine, others act on tyrosine, and a number (dual specific) act on all three. There are also protein kinases that phosphorylate other amino acids, including histidine kinases that phosphorylate histidine residues.

Phosphorylation usually results in a functional change of the target protein or substrate by changing enzyme activity, cellular location or association with other proteins.

Protein kinase inhibitors are types of enzyme inhibitors which specifically block the action of protein kinases. There is an entire range available for purchase and the selection of a protein kinase inhibitor involves a consideration of its specificity, permeability and stability. Moreover, protein kinase inhibitors may be reversible or irreversible depending upon whether the binding action of the protein kinase inhibitor to its target or substrate can be reversed.

STATEMENTS OF INVENTION

The invention herein described, according to a first aspect, therefore concerns the new use of at least one protein kinase inhibitor to detect cells of the immune system and in particular T cells.

Notably, the invention can be used in relation to either CD4+ or CD8+ Tcells and so reference herein to T cells includes reference to both CD4+ and CD8+ Tcells. Further, the invention has application in relation to T cells that bind, via their TCR, all forms of T cell ligands and in particular multimerized ligands.

The process of detection may particularly but not exclusively, involve the enhanced performance of an existing system for detection such as the enhanced staining with pMHC multimers and so subsequent imaging of immune cells, such as T cells. Reference herein to pMHC multimers, be they tetramers, pentamers, octomers or dextramers, or some other multimeric scaffold, includes reference to pMHC class I and pMHC class II.

Most notably still, the invention also relates to other TCR associated MHC ligands and so to other MHC-restricted T cells such as, without limitation, HLA A, B, C or E-restricted T cells, including CD1d-restricted T cells and T cells restricted by HLA class II molecules such as HLA DR, DQ and DP alleles.

Further the invention has application in the detection or sorting of T cells from any mammalian species including, without limitation, man, mice and monkey and also the conservation of reagent when detecting or sorting cells from any of said mammalian species.

In a preferred embodiment of the invention the new use involves the enhanced detection, or staining, of cell surface markers of the said cells and in particular T cells and, more particularly, the enhanced detection or staining of protein kinase sensitive cell surface markers such as T cell surface receptors (TCR's). Yet more ideally, the new use involves the binding of more TCR's with the chosen detection or staining agent(s).

Reference herein to the term protein kinase sensitive includes reference to a cell surface marker that binds less favourably to its detecting or staining agent in the presence of protein kinase enzymes and so can be made to bind more favourabley to said agent in the presence of a protein kinase inhibitor.

Whilst not wanting to be constrained or limited by any explanation of the underlying mechanism of the invention, we believe that a protein kinase inhibitor prevents the phosphorylation of cell surface markers, such as receptors, and in particular TCR's, by their relevant kinase and so prevents receptor internalization and recycling. This means more cell surface markers, or receptors, are available at the cell surface for detection or staining by a detection or staining agent, thus increasing the intensity or sensitivity of the detection or staining process.

Importantly, the benefits of the invention apply only to T-cells that express specific TCRs; PKI treatment does not result in the staining of T-cells that bear non-cognate TCRs.

In a further preferred embodiment of the invention said use comprises the step of pre-treating a population of cells to be detected with at least one protein kinase inhibitor before exposing said population to at least one agent for detecting or staining same.

Alternatively, the said use may comprise the step of treating a population of cells to be detected with at least one protein kinase inhibitor at the same time as exposing said population to at least one agent for detecting or staining same.

In either case, said protein kinase is ideally a reversible protein kinase meaning its binding action to its target site or substrate can be reversed. Ideally, said protein kinase inhibitor is a commercially available inhibitor such as, but not limited to any one or more of the following: Dasatinib, Lck inhibitor II, Wortmannin, Resveratrol, LY294002, AS604850, PI3-K alpha inhibitor 1 or PI3-K alpha inhibitor 2.

Moreover, the protein kinase inhibitor is, ideally, a tyrosine protein kinase inhibitor.

In a yet further preferred embodiment of the invention said treatment comprises the step of exposing said population of cells to said inhibitor for a period of time up to one hour. One hour may be exceeded but the beneficial effects associated with said treatment are achieved before this time interval of more than one hour expires. Indeed, the beneficial effects are achieved within seconds of exposure but we have found it advantageous to treat said population with said inhibitor for approximately 30 mins at 37° C. More preferably still, we have found it advantageous to treat said population with an amount of inhibitor up to 300 nM and most preferably less than 200 nM such as, for example only, 100, 90, 80, 70, 60, 50, 40, 30, 20, or 10 nM.

The ability of our system to detect or stain more efficiently, and so allow us to visualize cells, and in particular T cells, with either a small number of cell surface markers or TCR's; or an average number of cell surface markers or TCR's but which have low avidity for the detecting or staining agent, enables us to detect or stain cells that would otherwise be undetectable using conventional techniques. As just one example, we are now able to detect T cells bearing TCR's with low affinity for the cognate pMHCI ligand that would otherwise be undetectable using pMHCI monomer or tetramer staining.

Thus, in a further aspect, our invention concerns a method of detecting cells of the immune system, and in particular T cells, which comprises the use of at least one protein kinase inhibitor.

The method of detection may, particularly but not exclusively, involve the enhanced performance of an existing system for detection such as the enhanced staining with pMHC tetramers/multimers and so subsequent imaging of immune cells, such as T cells.

In a preferred embodiment of the invention the method involves the enhanced detection, or staining, of cell surface markers of the said cells and in particular T cells and, more particularly, the enhanced detection or staining of protein kinase sensitive cell surface markers such as T cell surface receptors (TCR's). Yet more ideally, the method involves the binding of more TCR's with the chosen detection or staining agent(s).

In a further preferred method of the invention said method comprises the step of pre-treating a population of cells to be detected with at least one protein kinase inhibitor before exposing said population to at least one agent for detecting or staining same.

Alternatively, the said method may comprise the step of treating a population of cells to be detected with at least one protein kinase inhibitor at the same time as exposing said population to at least one agent for detecting or staining same.

In either case, said protein kinase is ideally a reversible protein kinase meaning its binding action to its target site can be reversed. Ideally, said protein kinase inhibitor is a commercially available inhibitor such as, but not limited to any one or more of the following: Dasatinib, Lck inhibitor II, Wortmannin, Resveratrol, LY294002, AS604850, PI3-K alpha inhibitor 1 or PI3-K alpha inhibitor 2.

Moreover, the protein kinase inhibitor is, ideally, a tyrosine protein kinase inhibitor.

In a yet further preferred method of the invention said treatment comprises the step of exposing said population of cells to said inhibitor for a period of time up to one hour. One hour may be exceeded but the beneficial effects associated with said treatment are achieved before this time interval of more than one hour expires. Indeed, the beneficial effects are achieved within seconds of exposure but we have found it advantageous to treat said population with said inhibitor for approximately 30 mins at 37° C. More preferably still, we have found it advantageous to treat said population with an amount of inhibitor up to 300 nM and most preferably less than 200 nM such as, for example only, 100, 90, 80, 70, 60, 50, 40, 30, 20, or 10 nM.

Using our invention we have been able to detect low avidity antigen-specific T cells. Indeed the benefits of our invention have been so striking that our invention can be used, advantageously, to conserve detecting or staining agents.

According to a yet further aspect our invention concerns a method for conserving agents when detecting cells of the immune system and in particular T cells.

In this further aspect of our invention the agents to be conserved comprise known detecting or staining agents for detecting selected cells such as T cells within a population of cells and, more specifically, antigen-specific cells such as T cells and so T cells that have TCR's specific for the agent to be used, for example, TCR's specific for an antigen presenting molecule or cell such as a pMHC: pMHCI or pMHC11 or Cd1d etc. in the form of a monomer or multimer.

In this aspect of the invention the method involves conserving agents by the enhanced performance of an existing system for detection such as the enhanced staining with pMHC tetramers/multimers and so subsequent imaging of immune cells, such as T cells.

In a further preferred method of the invention said conserving method comprises the step of pre-treating a population of cells to be detected with at least one protein kinase inhibitor before exposing said population to at least one agent for detecting or staining same.

Alternatively, the said method may comprise the step of treating a population of cells to be detected with at least one protein kinase inhibitor at the same time as exposing said population to at least one agent for detecting or staining same.

In either case, said protein kinase is ideally a reversible protein kinase meaning its binding action to its target site can be reversed. Ideally, said protein kinase inhibitor is a commercially available inhibitor such as, but not limited to any one or more of the following: Dasatinib, Lck inhibitor II, Wortmannin, Resveratrol, LY294002, AS604850, PI3-K alpha inhibitor 1 or PI3-K alpha inhibitor 2.

Moreover, the protein kinase inhibitor is, ideally, a tyrosine protein kinase inhibitor.

In a yet further preferred method of the invention said treatment comprises the step of exposing said population of cells to said inhibitor for a period of time up to one hour. One hour may be exceeded but the beneficial effects associated with said treatment are achieved before this time interval of more than one hour expires. Indeed, the beneficial effects are achieved within seconds of exposure but we have found it advantageous to treat said population with said inhibitor for approximately 30 mins at 37° C. More preferably still, we have found it advantageous to treat said population with an amount of inhibitor up to 300 nM and most preferably less than 200 nM such as, for example only, 100, 90, 80, 70, 60, 50, 40, 30, 20, or 10 nM.

Advantageously, the enhanced detection or staining afforded by our invention only applies to cells such as T cells that express antigen specific markers, such as TCR's, this means protein kinase treatment does not result in the detection or staining of cells, such as T cells, that bear non-cognate markers or TCR's.

Indeed, we show herein that PKI treatment lowers the TCR/pMHCI affinity threshold required for pMHCI tetramer binding by as much as 5 fold, thereby allowing the binding of pMHC tetramers to CD8+ T-cells that express TCRs with very weak affinities for pMHCI (>80-500 μM).

This simple and universally applicable procedure thereby enables the visualization of previously undetectable tumour-specific and autoreactive CD8+ T-cells with pMHCI tetramers through the preferential enhancement of low avidity interactions with TCRs at the cell surface.

Moreover, our invention comprises at least one further benefit in that it, not only increases the detection of a selected population of cells within a given population without affecting the detection or staining of cells bearing non-cognate cell surface markers, but it also reduces agent induced cell death.

In this latter respect, we have shown that the treatment with at least one protein kinase inhibitor reduces pMHCI multimer, and in our example tetramer, induced cell death.

According to a further aspect of the invention there is therefore provided the use of at least one protein kinase inhibitor for sorting, in a population of immune cells, a viable, selected, sub-population of cells. Ideally said cells are T cells.

According to a yet further aspect of the invention there is provided a method for sorting, in a population of immune cells, a viable, selected, sub-population of cells. Ideally said cells are T cells.

In the latter two aspects of the invention the use of at least one protein kinase inhibitor helps to ensure that a selected population of cells, typically T cells, with preferred, usually high affinity, TCR's are kept viable and, following cell sorting, are available for use.

In this further aspect of the invention the method of sorting may involve the enhanced performance of an existing system for sorting such as the enhanced sorting with pMHC tetramers/multimers and so the sorting of immune cells, such as T cells.

In a further preferred method of the invention said sorting method comprises the step of pre-treating a population of cells to be sorted with at least one protein kinase inhibitor before exposing said population to at least one agent for sorting or detecting same.

Alternatively, the said method may comprise the step of treating a population of cells to be sorted with at least one protein kinase inhibitor at the same time as exposing said population to at least one agent for sorting or detecting same.

In either case, said protein kinase is ideally a reversible protein kinase meaning its binding action to its target site can be reversed. Ideally, said protein kinase inhibitor is a commercially available inhibitor such as, but not limited to any one or more of the following: Dasatinib, Lck inhibitor II, Wortmannin, Resveratrol, LY294002, AS604850, PI3-K alpha inhibitor 1 or PI3-K alpha inhibitor 2.

Moreover, the protein kinase inhibitor is, ideally, a tyrosine protein kinase inhibitor.

In a yet further preferred method of the invention said treatment comprises the step of exposing said population of cells to said inhibitor for a period of time up to one hour. One hour may be exceeded but the beneficial effects associated with said treatment are achieved before this time interval of more than one hour expires. Indeed, the beneficial effects are achieved within seconds of exposure but we have found it advantageous to treat said population with said inhibitor for approximately 30 mins at 37° C. More preferably still, we have found it advantageous to treat said population with an amount of inhibitor up to 300 nM and most preferably less than 200 nM such as, for example only, 100, 90, 80, 70, 60, 50, 40, 30, 20, or 10 nM.

Our invention will now be exemplified by reference to the following Materials and Methods and Results wherein:—

FIG. 1: Dasatinib (PKI) substantially improves pMHC tetramer staining intensity. A. $10^5$ ILA1 CTL were re-suspended in 40 μl of PBS±50 nM dasatinib or Lck inhibitor II (PKI's) (Calbiochem), then incubated at 37° C. for 30 minutes. Cells were then stained with cognate HLA A2/ILAKFLHWL (SEQ ID NO:1)-PE (pMHC) tetramer at a final concentration of 10 μ/ml for 20 minutes at 37° C., washed twice in PBS and analyzed on a FACSCalibur (BD) flow cytometer. A >10-fold increase in median fluorescence intensity (MFI) was observed after treatment with 50 nM dasatinib (Das+Tet) or LcK inhibitor II (Lck II+Tet) compared to staining without PKI pre-treatment (Tet only). B. $10^5$ ILA1 CTL were treated with various concentrations of dasatinib for 30 minutes at 37° C., then stained with either HLA A2/ILAKFLHWL (SEQ ID NO:1) tetramer or the non-cognate HLA A2/ELAGIGILTV (SEQ ID NO:2) tetramer for 20minutes at 37° C. before washing with PBS. C. $10^5$ ILA1 CTL were resuspended in 40 μl of PBS± the indicated concentration of dasatinib and incubated for 60minutes at 37° C. Cells were then stained with cognate HLA A2/ILAKFLHWL (SEQ ID NO:1)-PE tetramer at a final concentration of 10 μg/ml for 20 minutes at 37° C. and washed twice in PBS prior to flow cytometric analysis. D. As (A), but ILA1 CTL were incubated with 50nM dasatinib for various times prior to staining. E. As (A), but tetramer concentration was varied to stain CTL pre-treated ±50 nM dasatinib for 30 minutes. F. $10^5$ Mel13 CTL were stained with various concentrations of HLA A2/ELAGIGILTV (SEQ ID NO:2) tetramer following incubation ±50nM dasatinib for 30 minutes. G. $5\times10^5$ splenocytes from an F5 TCR transgenic Rag$^+$ mouse were resuspended in PBS±50nM dasatinib and incubated for 30 minutes at 37° C. Cells were subsequently stained with H2-D$^b$/ASNENMDAM (SEQ ID NO: 7)-PE tetramer for 20 minutes at 37° C. followed by anti-CD8 Cy5.5 for 30 minutes on ice prior to two washes in PBS and analysis by flow cytometry. H. $10^5$ cells of the HLA DR*0101-restricted, influenza virus A HA$_{307-319}$ PKYVKQNTLKLAT (SEQ ID NO:8)-specific CD4$^+$ clone C6 were incubated with PBS±50 nM dasatinib for 30 minutes at 37° C., then stained with cognate PE-conjugated tetramer for 20minutes at 37° C. Samples were washed with PBS before flow cytometric analysis. Irrelevant tetramer was used as a negative control in all cases.

FIG. 2: Dasatinib treatment preferentially increases the ability of pMHCI tetramers to stain T-cells bearing low affinity TCRs. A. $10^5$ ILA1 CTL were stained with 10 μg/ml PE-conjugated HLA A2 tetramer folded around the 8E, 5Y, 4L, index (ILAKFLHWL(SEQ ID NO:1)), 3G8T or 3G peptides for 20 minutes at 37° C. following incubation ±50nM dasatinib for 30minutes at 37° C. For all samples, data were acquired with a FACSCalibur flow cytometer (BD) and analyzed using FlowJo software. Irrelevant tetramer was used as a negative control. B. The MFI of tetramer staining for all of the variants in the presence and absence of dasatinib displayed in (A) are plotted against the monomeric affinity of TCR/pMHCI interactions previously measured for each of these variants expressed as the dissociation constant ($K_D$) (Table 1). Curves were fitted as described in the Materials and methods.

Figure 3:
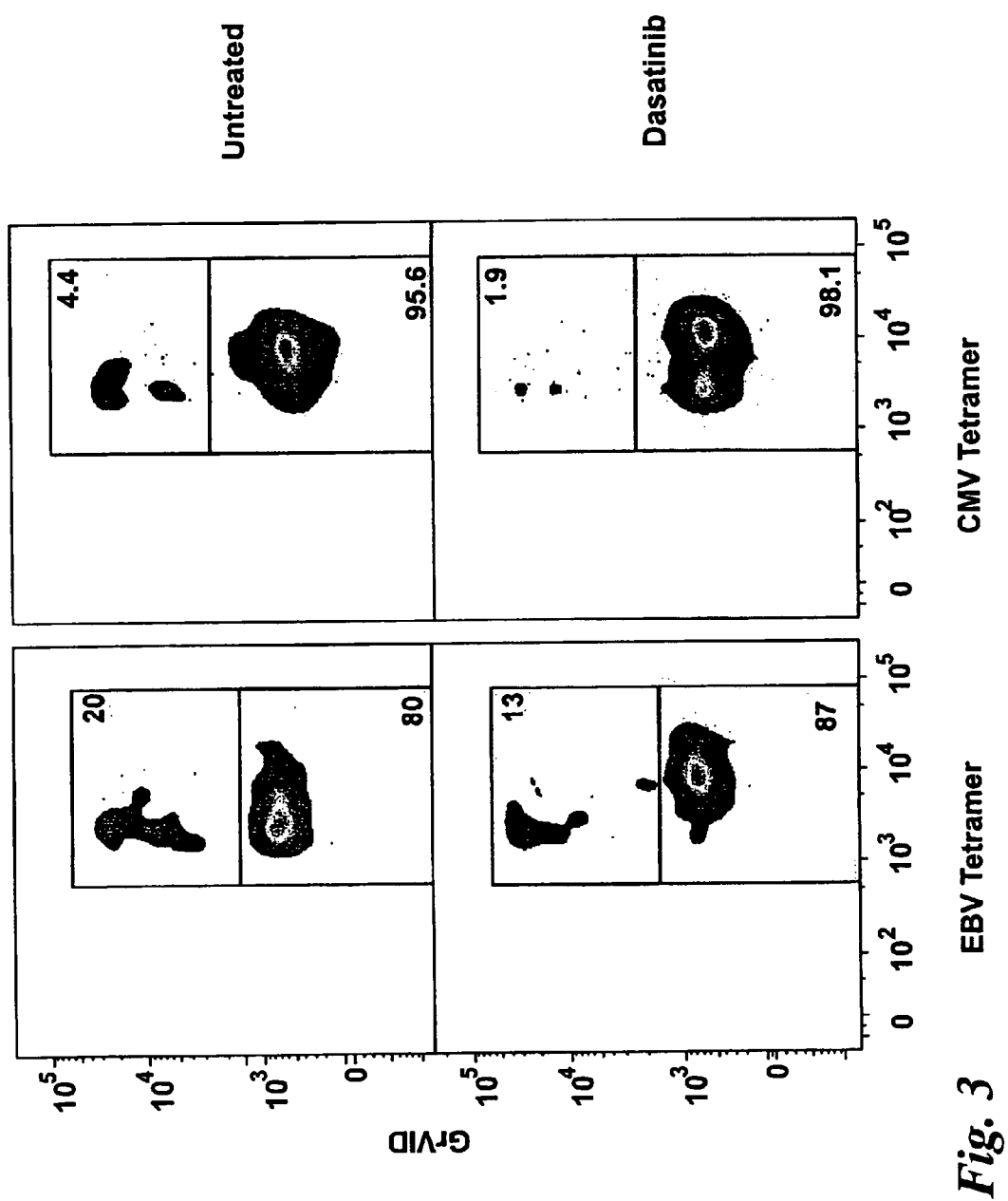

FIG. 3: Dasatinib reduces pMHCI tetramer-induced cell death. Increased tetramer staining in the presence of dasatinib appears to be due partly to reduced cell death. It is known that pMHCI tetramer-induced signaling can trigger cell death (Purbhoo et al., 2001; Xu et al., 2001; Guillaume et al., 2003; Cebecauer et al., 2005). Cell death induced by tetramer staining was assessed using the amine-reactive viability dye GrViD at the end of the staining procedure, which is spectrally distinct from ViViD. PBMC were stained with ViViD to identify and allow exclusion of dead and dying cells prior to the addition of pMHCI tetramer; GrVID staining was performed after pMHCI tetramer and surface antibody staining. Data were acquired on a BD LSR II flow cytometer and analyzed using FlowJo software. ViViD$^±$, CD14$^+$ and CD19$^+$ cells were excluded from the analysis and the frequency of GrViD-positive cells was assessed in the tetramer-positive CD3+CD8$^+$ T-cell populations. Representative flow profiles are shown here for CD$^+$T-cells specific for the HLA A2-restricted epitopes CMV pp65$_{495-503}$ (NLVPMVATV(SEQ ID NO:3)) and EBV BMLFI$_{259-267}$ (GLCTLVAML SEQ ID NO:4)). The frequencies of dead cells varied depending on the tetramer used, but the frequency of GrViD-positive dead cells within the tetramer-positive population was always lower in the presence of 50 nM dasatinib. These data, together with comparable results in other systems (data not shown), suggest that the cumulative cell death over the time course of a staining experiment could be substantially reduced by treatment with dasatinib.

FIG. 4: Dasatinib enhances the visualization of antigen-specific CM8$^+$ T-cells in mixed cell populations. A. Staining of HLA A2-restricted CTL lines expanded from PBMC by one round of stimulation with the influenza matrix M1$_{58-66}$ peptide (GILGFVFTL(SEQ ID NO:5)) or the Melan-A/Mart-1$_{26-35}$ peptide (ELAGIGILTV(SEQ ID NO:2)). Lines were stained with cognate tetramer ± pre-treatment with 50 nM dasatinib for 30 minutes at 37° C. B. Flow cytometric profiles of live CD3$^+$ lymphocytes stained with HLA A2 tetramers folded around the EBV BMLF1$_{259-267}$ (GLCTLVAML(SEQ ID NO:4)), CMV pp65$_{495-503}$ (NLVPMVATV(SEQ ID NO:3)) or Melan-A/Mart-1$_{26-35}$ (ELAGIGILTV(SEQ ID NO:2)) peptide epitopes. $2\times10^6$ PBMC were stained with the amine-reactive viability dye ViViD, then stained with tetramer (1 μg in minimal staining volume) ±pre-treatment with dasatinib for 30 minutes at 37° C. Cells were then stained with cell surface markers as described in the Materials and Methods; a dump channel was used to exclude dead cells, CD14$^+$ and CD19$^+$ cells from the analysis. Boolean gating was carried out to exclude aggregates. Data were acquired with a BD LSR II flow cytometer and analyzed using FlowJo software.

FIG. 5: Dasatinib allows detection of autoreactive CTL. A. CTL clone IE6, specific for the HLA A2-restricted epitope PPI$_{15-24}$, was activated with either CMV pp65$_{495-503}$ or PPI$_{15-24}$ peptide for 6 hours at 37° C. and then assayed for TNFα production by intracellular cytokine staining as detailed in the Materials and Methods. B. Staining of CTL clone IE6 with either an irrelevant or HLA A2/PPI$_{15-24}$ tetramer±pre-treatment with 50 nM dasatinib for 30 minutes at 37° C. C. Representative stainings with HLA A2/PPI$_{15-24}$ tetramer±pre-treatment with 50 nM dasatinib for 30 minutes at 37° C. Left panels: control subject PBMCs; middle panels: type I diabetic patient PBMCs; right panels: a short-term line expanded by one round of peptide stimulation from a type 1 diabetic patient.

Figure 6:
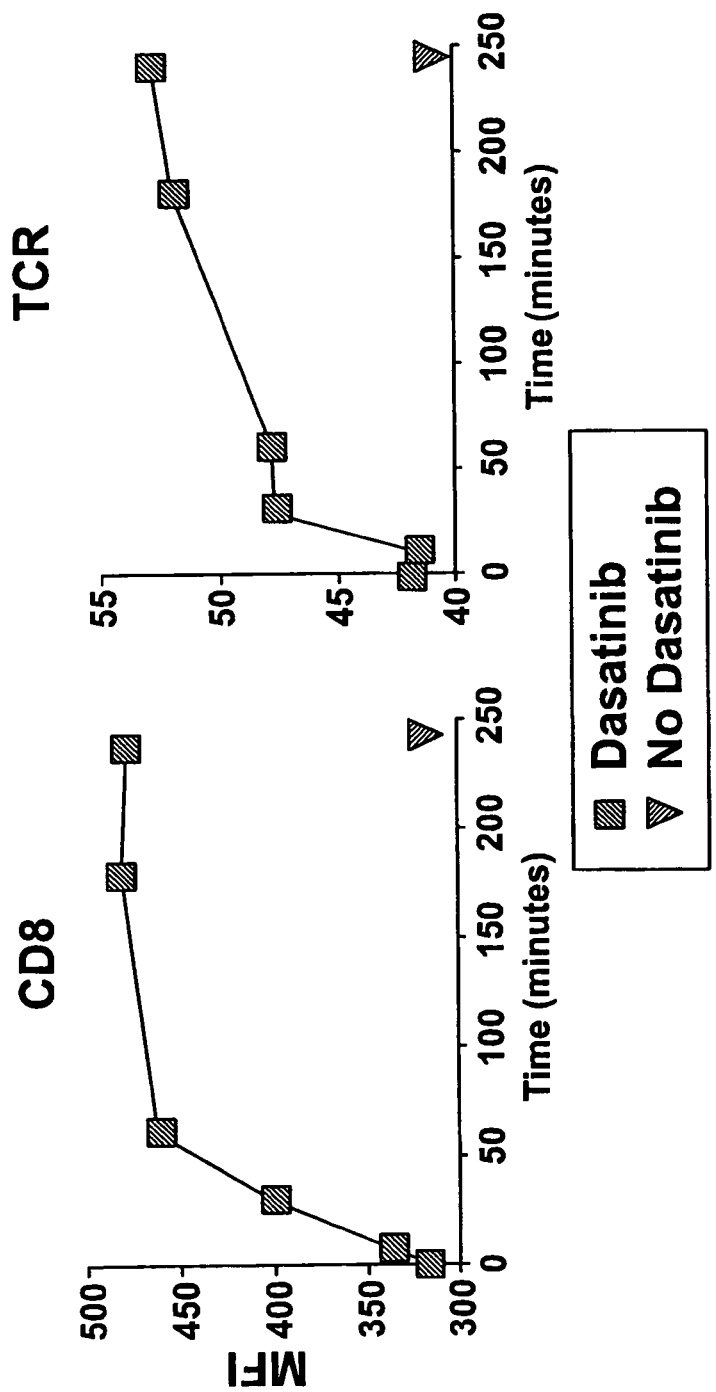

FIG. 6: Dasatinib results in a time dependent increase in TCR and CD8 expression levels at the CTL cell surface. The ILA1 CTL clone was treated with PBS±50 nM dasatinib at 37° C. and $10^5$ CTL were removed from the medium at 0, 10, 30, 60, 180 and 250 minutes. CTL were subsequently stained with anti CD8 FITC (clone SKI; BD, Pharmingen; left panel) or anti-TCR FITC (clone BMA 031; Serotec; right panel) for 30 minutes on ice, washed twice and resuspended in PBS. Data were acquired on a FACSCalibur flow cytometer (BD) and analyzed using FlowJo software.

Figures 7A, 7B:
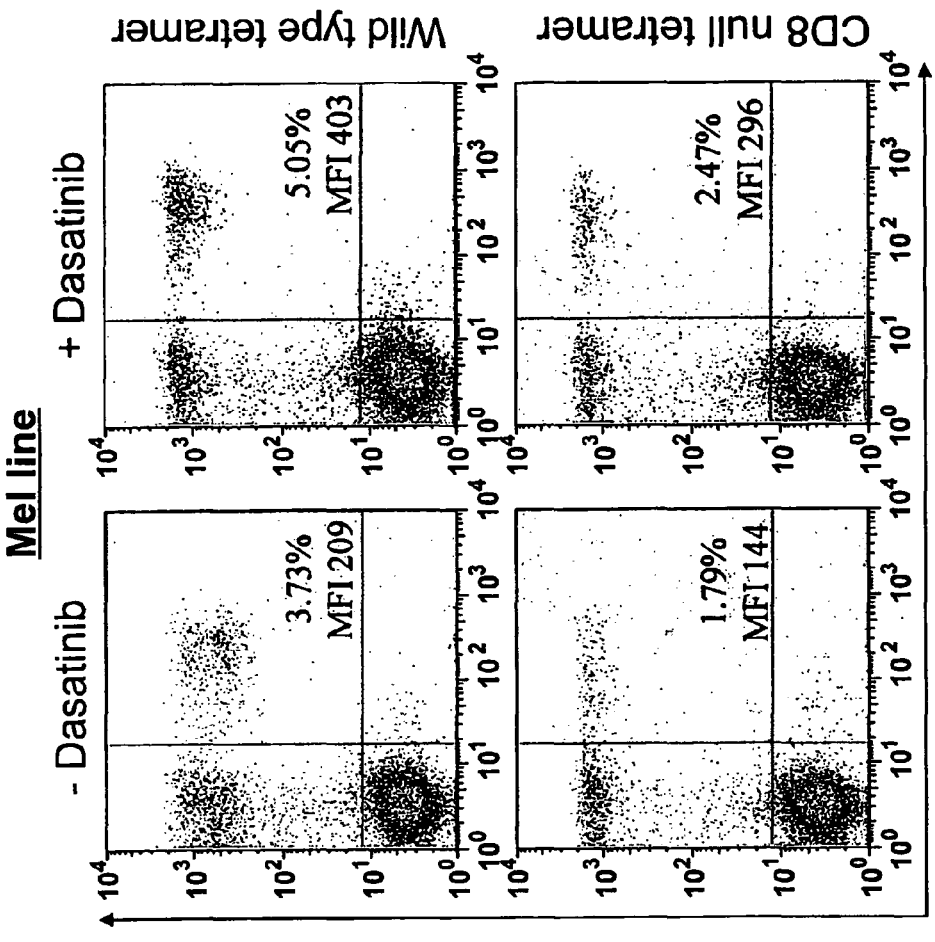

FIG. 7: Beneficial effects of dasatinib effects are not CD8-mediated. A. Melc5 CTL were pre-treated with PBS±50nM dasatinib for 30 minutes at 37° C., then stained with HLA A2 DT227/8KA cognate tetramer for 20 minutes at 37° C. After washing twice, data were acquired on a FACSCalibur flow cytometer (BD) and analyzed using FlowJo software. B. Staining of HLA A2-restricted CTL lines expanded from PBMC by one round of stimulation with the Melan-A/Mart-1$_{26-35}$ peptide (ELAGIGILTV(SEQ ID NO:2)). Lines were stained with either wild type or CD8 null cognate tetramer ± pre-treatment with 50 nM dasatinib for 30 minutes at 37° C.

Figure 8A:
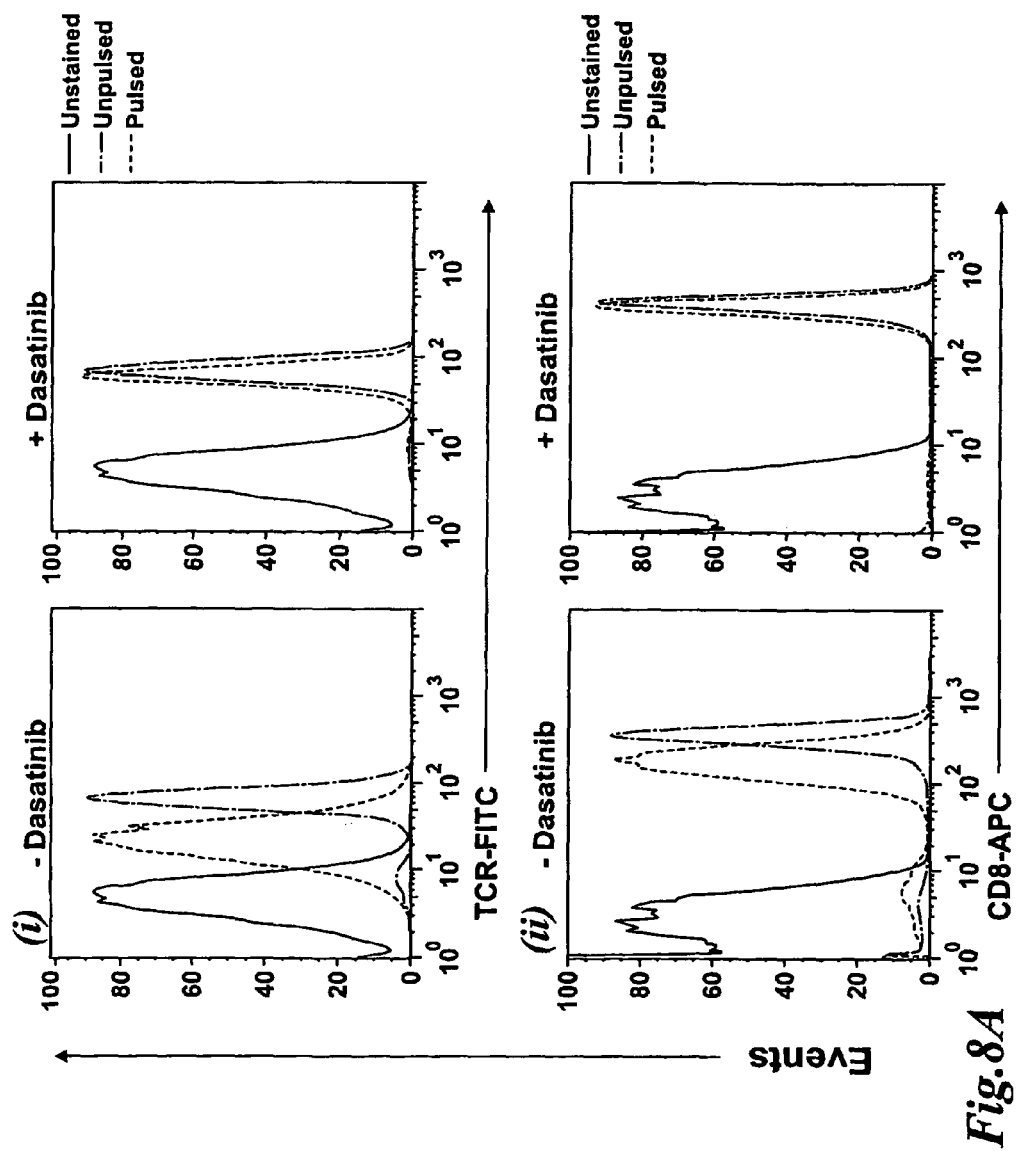

FIG. 8: Dasatinib blocks antigen-induced TCR downregulation and tetramer internalization from the cell surface. A. Mel13 CTL were pre-treated with PBS±50 nM dasatinib and exposed to C1R-A2 B cells previously pulsed with $10^{-6}$M ELAGIGILTV (SEG ID NO:2) peptide or medium alone for 4 hours at 37° C. Cells were subsequently stained with anti-TCR-FITC (clone BMA 031; Serotec) and anti-CD8-APC (clone RPA-T8; BD Pharmingen) mAbs for 30 minutes on ice, washed twice and resuspended in PBS. Data were acquired on a FACSCalibur flow cytometer (BD) and analyzed using FlowJo software. B. $10^5$ ILA-1 CTL were pre-treated with PBS (i & ii) or PBS+50 nM dasatinib (iii & iv) for 30 minutes at 37° C., then stained with 20 μg/ml HLA A2/IL-AKFLHWL (SEQ ID NO:1)-Alexa488 tetramer for 15 minutes at 37° C. Microscopy was performed as described in the Materials and Methods.

Figure 9:
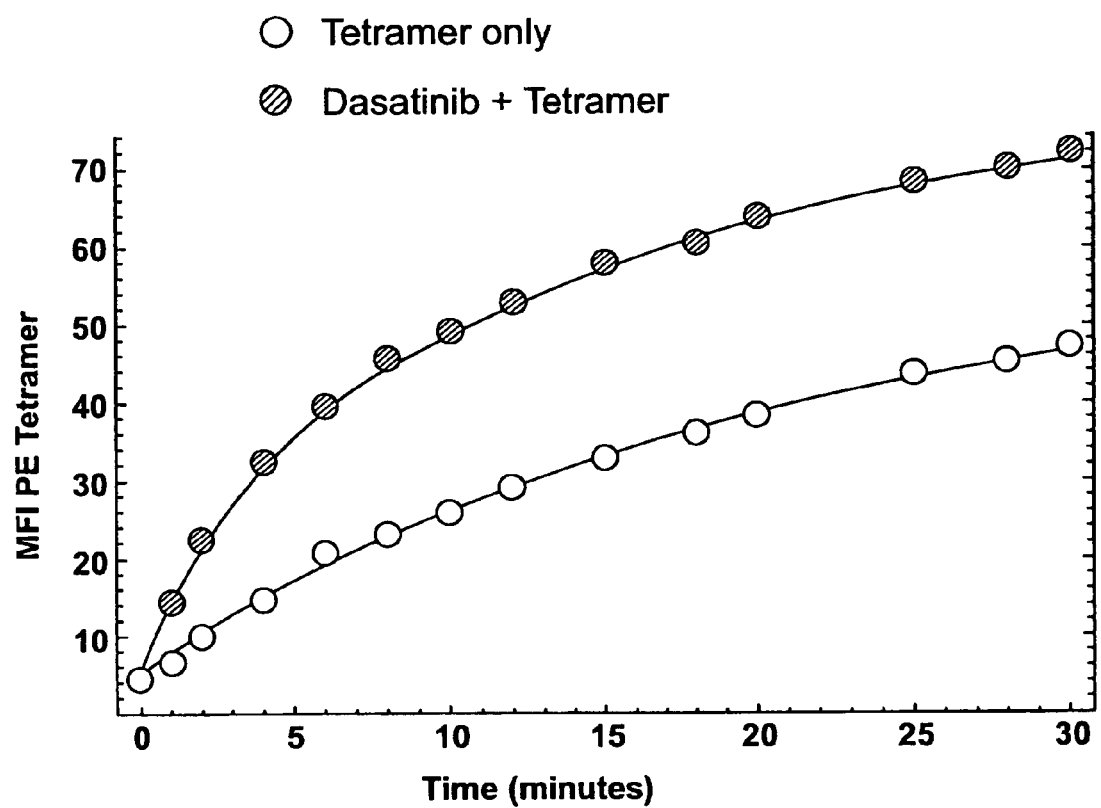

FIG. 9: Dasatinib enhances pMHCI tetramer on-rate. Rate of HLA A2/hTERT$_{540-548}$ (ILAKFLHWL(SEQ ID NO:1)) tetramer recruitment to the cell surface of clone ILA1 is substantially enhanced following treatment of CTL with 50 nM dasatinib for 30 minutes at 37° C. Subsequent to treatment with dasatinib, on-rate experiments were performed and analyzed as described previously (Laugel et al., 2007). Curves represent the following rate estimates: fast rate 0.14/min, slow rate 0.04/min (tetramer only); fast rate 0.42/min, slow rate 0.06/min (dasatinib+tetramer).

Figure 10:
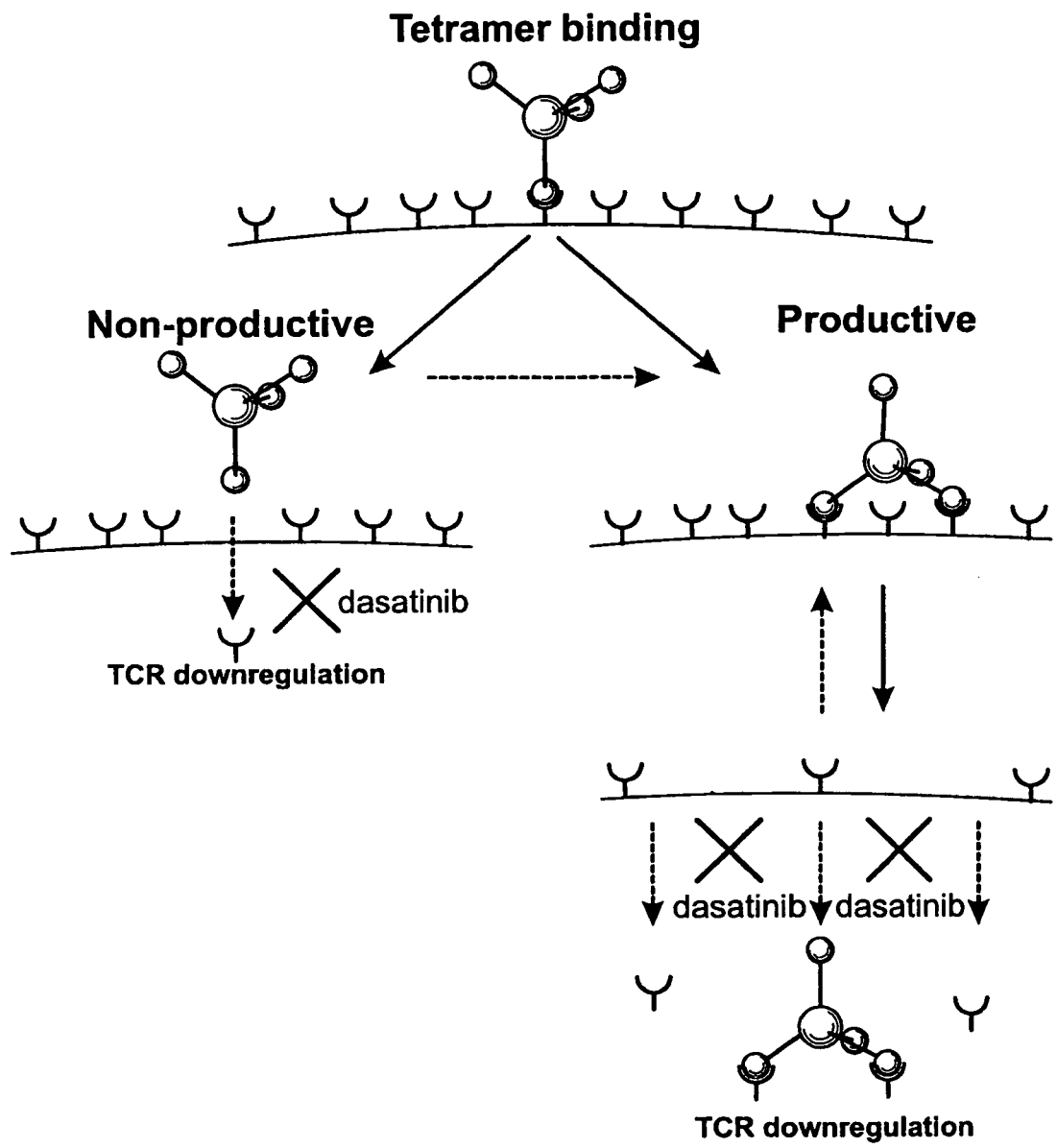

FIG. 10: Dasatinib prevents down-regulation of 'empty' TCRs. Proposed model for the mechanism by which dasatinib enhances cognate tetramer staining. Dasatinib treatment prevents TCR and coreceptor down-regulation and maintains these receptors at the cell surface, thereby increasing molecular availability for further capture of pMHC tetramer from solution.

MATERIALS AND METHODS 2.1 Cells

The ILA1 CTL clone is specific for the HLA A*0201 (HLA A2 from hereon) restricted human telomerase reverse transcriptase (hTERT) epitope ILAKFLHWL (SEQ ID NO:1) (hTERT$_{540-548}$). Mel13 and Mel5 CTL clones are specific for the HLA A2 restricted Melan-A$_{26-35}$ epitope ELAGIGILTV (SEQ ID NO:2). ILA1, Mel5 and Mel13 CD8$^+$ cytotoxic T lymphocyte (CTL) clones were generated and re-stimulated as described previously (Whelan et al., 1999; Laugel et al., 2005). CTL were maintained in RPMI 1640 (Gibco) supplemented with 100 U/ml penicillin (Gibco), 100 μg/ml streptomycin (Gibco), 10% heat inactivated fetal calf serum (FCS; Gibco), 2.5% Cellkines (Helvetica Healthcare, Geneva), 200 IU/ml IL-2and 25 ng/ml IL-15 (Peprotech). CTL lines specific for the influenza matrix protein M1$_{58-66}$ (GILGFVFTL (SEQ ID NO:5)) and Melan-A$_{26-35}$ (ELAGIGILTV(SEQ ID NO:2)) epitopes, both restricted by human leukocyte antigen (HLA) A*0201 (HLA A2 from hereon), were generated by pulsing 6×10$^6$ PBMC from an HLA A*0201$^+$ individual with cognate peptide at concentrations of 1 μM and 100 μM, respectively, for 1 hour at 37° C.; cells were subsequently washed and resuspended in RPMI 1640 supplemented with 100 U/ml penicillin (Gibco), 100 μg/ml streptomycin (Gibco) and 10% heat inactivated FCS (Gibco) only. After 3 days, increasing amounts of IL-2 were added to the media reaching a maximum concentration of 20IU/ml by day 14; lines were then tested by pMHCI tetramer staining. Patient samples were collected by leukapheresis; mononuclear cells were isolated by standard Ficoll-Hypaque density gradient centrifugation and stored by cryopreservation. For autoimmune studies, blood was obtained from two HLA-A2$^+$ patients with type 1 diabetes; both were adults, aged 27 and 31 years, and were studied within 3 months of diagnosis. Short-term lines from these diabetic patients were established as described above using the PPI$_{15-24}$ autoantigen preproinsulin peptide (ALWGPDPAAA(SEQ ID NO:6)); this peptide bind HLA-A2 with high affinity (Arif et al., 2004). Naïve murine CTL were obtained by harvesting splenocytes from transgenic F5 Rag$^+$ mice. A significant percentage of CD8$^+$ T-cells within the splenic populations of these mice express the F5 TCR, which recognizes the H-2D$^b$-restricted influenza H17-derived nucleoprotein peptide epitope ASNENMDAM (SEQ ID NO:7) (Mamalaki et al., 1993). The HLA DR*0101-restricted CD4$^+$ T-cell clone C6 recognizes the influenza virus A HA$_{307-319}$ epitope (PKYVKQNTLKLAT(SEQ ID NO:8)).

2.2 Protein Kinase Inhibitors

Dasatinib was synthesized as described previously (Lombardo et al., 2004). Biological activity was tested in a cell death titration assay on BA/F3 bcr-abl cells as described previously (Magnusson et al., 2002). Dasatinib was dissolved in DMSO to a concentration of 1 mM and stored in aliquots at −20° C. Once thawed, these stocks of dasatinib were stored at 4° C. and used within 7 days. The 1 mM DMSO stock was diluted 1/10,000 in PBS on the day of experimentation to achieve a working solution of 100 nM; subsequent ½ dilution yielded a final concentration of 50 nM in cellular assays unless stated otherwise. The 100 nM working solution was always made up on the day of experimentation as the shelf-life of this solution is short (~days). Staurosporine (Biomol), Lck inhibitor II (Calbiochem), genestein (calbiochem), herbimycin A (Calbiochem), PP2 (Calbiochem) and PP3 (Calbiochem) were dissolved and stored at −20° C. in DMSO. PKIs were dissolved in PBS prior to use and tested at concentrations of 1 nM, 3 nM, 5 nM, 10 nM, 20 nM, 50 nM, 100 nM, 250 nM, 500 nM and 1 μM.

2.3 pMHCI Tetramer Manufacture

Soluble biotinylated pMHCI monomers were produced as described previously (Wooldridge et al., 2005). Tetrameric pMHCI reagents were constructed by the addition of either R-Phycoerythrin (PE)-conjugated streptavidin (Molecular Probes, Invitrogen) or Alexa 488-conjugated streptavidin (Molecular Probes, Invitrogen) at a pMHCI:streptavidin molar ratio of 4:1. Conjugated streptavidin was added to a solution of soluble pMHCI in 5 equal aliquots at 20 minute intervals and subsequently stored in the dark at 4° C.

2.4 pMHCI tetramer staining and flow cytometry: clones and splenoctyes 10$^5$ Mel13, Mel5 or ILA1 CTL were pre-treated at 37° C. with dasatinib at a range of concentrations (0-50nM) for a series of durations up to 1 hour. Mel13/Mel5 or ILA1 were then stained with either PE-conjugated HLA A2/ELAGIGILTV (SEQ ID NO:2) or HLA A2/ILAKFLHWL (SEQ ID NO:1) tetramer, respectively, at a final concentration of 10 μg/ml for 20 minutes at 37° C. The HLA DR*0101-restricted clone C6 was stained with HLA DR*0101/PKYVKQNTLKLAT (SEQ ID NO:8) PE tetramer for 20 minutes at 37° C. After initial experiments to determine the optimal conditions of use, all subsequent experiments were performed by incubating T-cells ±50nM dasatinib for 30 minutes at 37° C. prior to tetramer staining. The HLA DR*0101-restricted clone C6 was stained with HLA DR*0101/PKYVKQNTLKLAT (SEQ ID NO:8) PE tetramer. Subsequent to tetramer staining, CTL clones were stained with anti-human CD8-FITC (clone SK1; BD Pharmingen) and 7-AAD (Viaprobe; BD Pharmingen) for 30 minutes on ice then washed twice with phosphate buffered saline (PBS); the HLA DR*0101-restricted clone C6 was stained with 7-AAD (Viaprobe; BD Pharmingen) only. For murine CTL, 5×10$^5$ splenocytes were pre-treated with 50 nM dasatinib for 30 minutes at 37° C., stained with H2-D$^b$/ASNENMDAM (SEQ ID NO:7) PE-conjugated tetramer for 20 minutes at 37° C. and then anti-murine CD8-Cy5.5 for 30 minutes on ice, washed twice and re-suspended in PBS. Data were aquired using a FACSCalibur flow cytometer (BD) and analyzed using FlowJo software (Treestar Inc., Ashland, Oreg. USA).

2.5 pMHCI tetramer staining and flow cytometry: human peripheral blood mononuclear cells Frozen peripheral blood mononuclear cells (PBMCs) were thawed in a 37° C. water bath until a small clump of ice remained and then transferred into RPMI medium containing 10% FCS, 100 U/ml penicllin, 100 μg/ml streptomycin, 2 mM L-glutamine (Gibco) and 100 U DNase/ml (Roche Diagnostics Corporation, Indianapolis, Ind. USA). PBMC were washed twice in this medium and then left to rest for 2 hours at 37° C. After 2 washes with PBS, 2×10$^6$ PBMC were stained with live/dead® fixable violet amine reactive dye (Invitrogen Corporation, Carlsbad, Calif., USA), washed and incubated for 30 minutes at 37° C. in PBS alone or PBS containing 50 nM dasatinib. Subsequently, PBMC in 50 µl of PBS alone or PBS containing 50 nM dasatinib were stained for 20 minutes with pHLA A2 tetramers refolded around either CMV pp65$_{495-503}$ (NLVPMVATV SEQ ID NO:3), EBV BMLF1$_{259-267}$ (GLCTLVAML SEQ ID NO:4) or Melan-A/Mart-1$_{26-35}$ (ELAGIGILTV(SEQ ID NO:2)) peptides. After 2 washes in PBS containing 1% FCS and 0.02% sodium azide (Sigma-Aldrich, St. Louis, Mo. USA), cells were stained with a selection of the following cell surface monoclonal antibodies (mAbs): (i) anti-CD3-APC-Cy7 and anti-CD8-APC (BD Biosciences, San Jose, Calif., USA); (ii) anti-CD4-PE-Cy5.5 (Caltag Laboratories, purchased through Invitrogen Corporation, Carlsbad, Calif., USA); and, (iii) anti-CD8-quantum dot (QD)705, anti-CD14-Pacific Blue and anti-CD19-Pacific Blue, conjugated in-house according to standard protocols (http://drmr.com/abcon/index.html). The latter two mAbs were used to exclude CD14$^+$ monocytes and CD19$^+$ B cells, which can bind tetramer non-specifically, from the analysis. Finally, cells were washed and resuspended in PBS containing 1% paraformaledehyde (PFA). Stained PBMC were acquired on a BD LSR II (Becton Dickinson Immunocytometry Systems, San Jose, Calif., USA) and analyzed using FlowJo software (Tree Star, Inc., Ashland, Oreg., USA).

2.6 TCR downregulation and tetramer on-rate experiments

HLA A2-expressing C1R B cells (Hutchinson et al., 2003) were either pulsed with ELAGIGILTV (SEQ ID NO:2) peptide at a concentration of 10$^{-6}$M for 60 minutes at 37° C. or incubated in medium alone. After two washes with RPMI 1640 supplemented with 100 IU/ml penicillin and 100 µg/ml streptomycin, 60,000 HLA A2$^+$ C1R cells (pulsed or unpulsed) were incubated for 4 hours at 37° C. with 30,000 Mel13 CTL that had been pre-treated with PBS±50 nM dasatinib for 30 minutes at 37° C. Cells were then stained with anti-TCR-FITC (clone BMA 031; Serotec) and anti-CD8-APC (clone RPA-T8; BD Pharmingen) for 30 minutes on ice, washed twice and resuspended in PBS. Data were acquired using a FACSCalibur flow cytometer and analysed using FlowJo software (Treestar Inc., Ashland, Oreg. USA). Tetramer on-rate experiments were performed as previously described (Laugel et al., 2007).

2.7 Fluorescence Microscopy

10$^5$ ILA1 CTL were treated with PBS±50 nM dasatinib for 30 minutes at 37° C., then stained with Alexa 488-conjugated (Molecular Probes) HLA A2/ILAKFLHWL (SEQ ID NO:1) tetramer at a final concentration of 20 µg/ml for 15 minutes at 37° C. Following two washes with PBS, each sample was fixed in 2% paraformaldehyde. After fixing, ILA1 CTL were re-suspended in 100 µl of 2% FCS/PBS and then spun on to a microscope slide at 550 rpm for 5 minutes using a cytospin. Samples were subsequently analysed on a Leica DM LB2 (Leica Microsystems) fluorescence microscope.

2.8 IFNγ ELISpot Assays

CD8$^+$ T-cell responses to islet autoantigen were detected by IFNγ ELISpot as described previously (Chang et al., 2003) with the following modifications. PBMCs were pre-cultured at 37° C./5% CO$_2$ in single wells of 48-well plates at a density of 1×10$^6$ cells in 0.5 ml TC medium (RPMI 1640 supplemented with antibiotics (Invitrogen) and 10% human AB serum (PAA, Somerset, UK)) containing the test peptide at a final concentration of 10 µM. Control wells contained TC medium with an equivalent concentration of diluent (DMSO). After 24 hours incubation, non-adherent cells were re-suspended using pre-warmed TC medium (2% AB serum), washed, brought to a concentration of 10$^6$ cells/300 µl, and then dispensed in 100 µl aliquots into wells of 96-well ELISpot plates (Nunc Maxisorp; Merck Ltd., Poole, UK) pre-blocked with 1% bovine serum albumin in PBS and pre-coated with monoclonal anti-IFNγ (U-Cytech, Utrecht, NL). Assays were then developed according to the manufacturer's instructions; plates were dried and spots were counted using a BioReader 3000 (BioSys, Karben, Germany) and reported as total responder cells per 10$^6$ PBMCs.

2.9 Intracellular Cytokine Staining Assays

10$^6$ CTL were stimulated with specific peptide at a concentration of 10 µg/ml for 6 hours; brefeldin A (10 µg/ml; Sigma-Aldrich) was added for the final 5 hours. Unrelated peptide (10 µg/ml) was used as a negative control. Briefly, the cells were fixed in paraformaldehyde (2%; Sigma-Aldrich), permeabilized with saponin (0.5%; Sigma-Aldrich), and labeled with APC-conjugated anti-TNFα mAb (BD Pharmingen). The cells were evaluated using a FACSCalibur flow cytometer (BD Biosciences). At least 10,000 events gated on forward and side scatter were analyzed using FlowJo software (Tree Star, Inc., Ashland, Oreg., USA). Corresponding isotype control antibodies were used to establish the quadrants for analysis.

2.10 Mathematical Modelling of the Dasatinib Effect on pMHCI Tetramer Staining

A mathematical model that relates staining intensity to tetramer binding kinetics has been described previously (Laugel et al., 2007; van den Berg et al., 2007). Briefly, in this model, the high binding avidity of pMHCI tetramers is accounted for by assuming that tetramers can engage up to three TCR molecules, forming a cluster of one, two, or three TCRs in which association and dissociation between the TCRs and the tetramer pMHCI sites occurs at a much higher rate than diffusive escape of temporarily unbound TCRs, tending to stabilize the cluster until the tetramer happens to become disassociated with TCR molecules at all four sites. Moreover, in singlet and duplet clusters, a free TCR can associate contacts with free pMHCI sites to form, respectively, a duplet or triplet cluster. The dasatinib effect is incorporated into this model by assuming that dasatinib alters the rate at which singlet and duplet clusters recruit free TCRs. Thus, the expression for the relative staining intensity I becomes:

$$I = I_{min} + \Delta_I ((K_1/K_D) r_0 + \delta_D (K_2/K_D)^3 r_0^2 + \delta_T^2 (K_3/K_D)^6 r_0^3)$$

where $K_D$ is the single-site dissociation constant; $K_1$, $K_2$ and $K_3$ are kinetic parameters; $I_{min}$ and $\Delta_I$ relate the read-out to the number of surface bound tetramers ($I_{min}$ is a nuisance parameter, representing the background level); $\delta_D$ is the duplet recruitment enhancement factor and $\delta_T$ is the triplet recruitment enhancement factor. In the absence of dasatinib, we have $\delta_D = \delta_T = 1$, whereas these factors are greater than 1 if dasatinib promotes TCR recruitment. The scaled free TCR density, $r_0$, is implicitly defined by the scaled conservation law:

$$1 = r_0 (K_1/K_D) r_0 + 2\delta_D (K_2/K_D)^3 r_0^2 + 3\delta_T^2 (K_3/K_D)^6 r_0^3$$

(from (Laugel et al., 2007)). Association kinetics has been found empirically to be described very well by the biphasic exponential model:

$$I(t) = I_{min} + I_{max,fast}(1 - \exp(\lambda_{fast} t)) + I_{max,slow}(1 - \exp(\lambda_{slow} t))$$

where I(t) is the staining intensity at time t and $I_{max,fast}$, $I_{max,slow}$, $\lambda_{fast}$, and $\lambda_{slow}$ are positive parameters (van den Berg et al., 2007). The goodness of fit is fair but not perfect; a better curve fit might be achieved with a more sophisticated model.

However, we have taken a minimalistic approach to modelling the dasatinib effect because of the mechanistic uncertainties surrounding its mode of action. The duplet recruitment enhancement factor $\delta_D$ was estimated to equal 6.53±2.93, whereas the triplet recruitment enhancement factor $\delta_T$ was estimated to equal 13.7±7.38 (by simultaneous non-linear least-squares). The fit of the model indicates that the data are consistent with the hypothesis that dasatinib makes free TCRs more readily available to pMHCI tetramers for recruitment into duplet and triplet clusters.

Figure 1B:
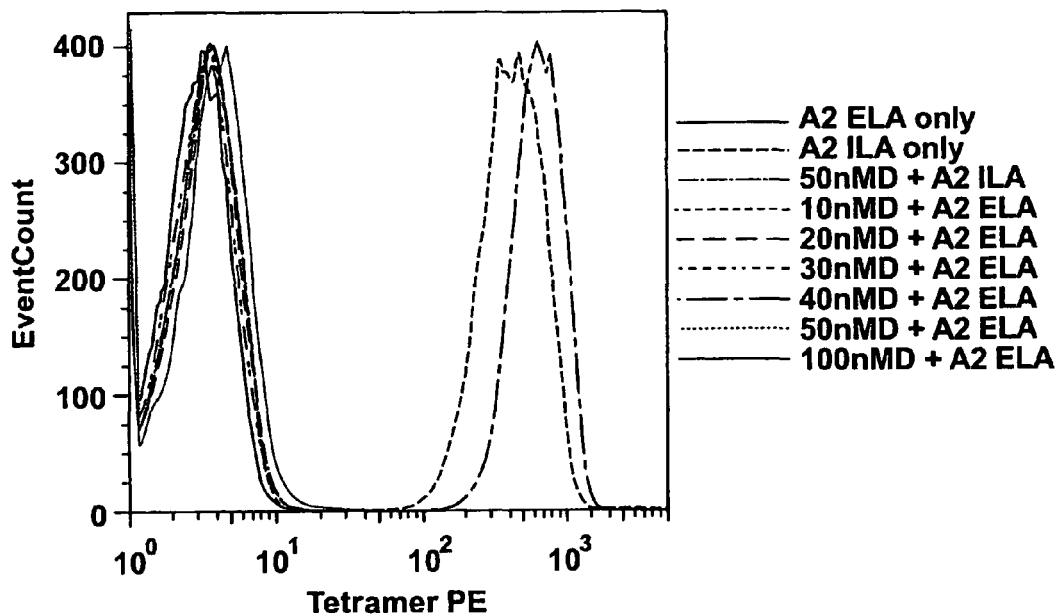

Results 3.1 PKI Treatment Enhances pMHC Tetramer Staining of $CD8^+$ and $CD4^+$ T-Cells Incubation of ILA1, a CTL clone specific for the HLA A2-restricted epitope $hTERT_{540-548}$ (ILAKFHWL), with the PKIs dasatinib or 3-(2-(1H-benzo[d]imidazol-1-yl)-6-(2-morpholinoethoxy)pyrimidin-4-ylamino)-4-methylphenol (Lck inhibitor II; Calbiochem) resulted in a >10 fold increase in pMHCI tetramer staining intensity (FIG. 1A). Pre-incubation with the PKI PP2 (Calbiochem) resulted in a moderate increase in tetramer staining; however, no significant enhancement was observed when CTL were pre-treated with herbimycin, PP3, genestein (Calbiochem) or staurosporine (Biomol) (data not shown). Importantly, PKI inhibitor treatment did not enhance staining with non-cognate pMHCI tetramer (FIG. 1B). Identical results were obtained for the HLA A2-restricted $Melan_{26-35}$ ELAGIGILTV (SEQ ID NO:2)-specific CTL clone Mel13 (data not shown).

Dasatinib is a reversible dual Src/Bcr-Abl kinase inhibitor with clinical applications that suppresses the activity of many kinases, including the Src protein kinase Lck ($IC_{50}$=0.4 nM) (Shah et al., 2004; Carter et al., 2005; Weichsel et al., 2008). Furthermore, while dasatinib reversibly inhibits antigen-specific T-cell effector functions, it is not toxic to T-cells in the short term at concentrations <100 nM (Weichsel et al., 2008). Indeed, T-cell clones incubated in 50 nM dasatinib for 24 hours were able to regain responsiveness to antigen within 1 hour of drug removal (data not shown). Dasatinib can also be used in flow cytometry-based applications without loss of cell viability (Weichsel et al., 2008). These properties prompted us to select dasatinib for further investigation in the current study.

Figure 1C:
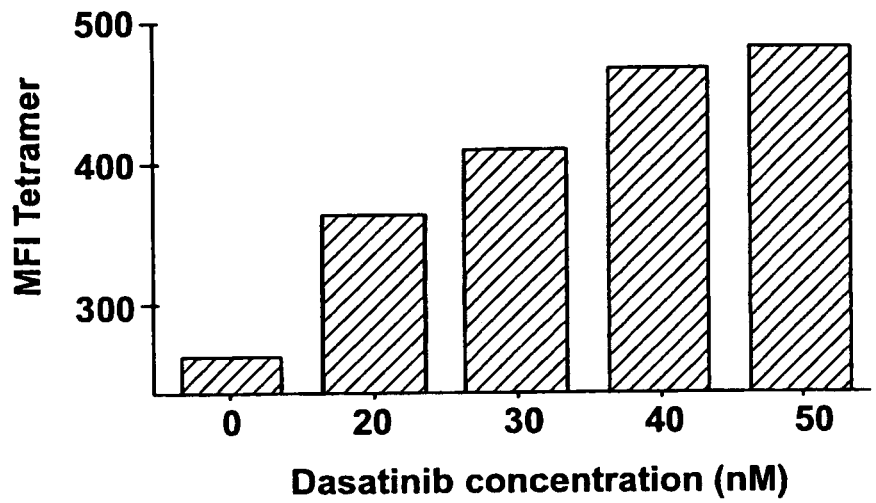
Figure 1D:
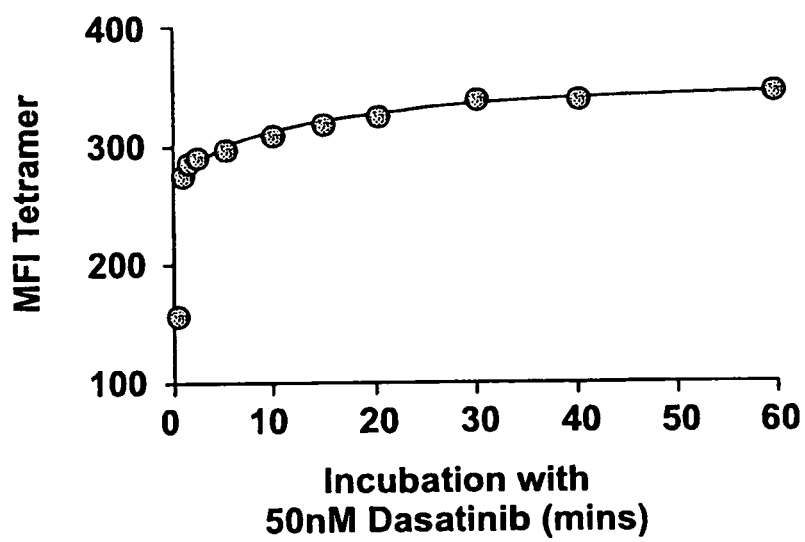
Figure 1E:
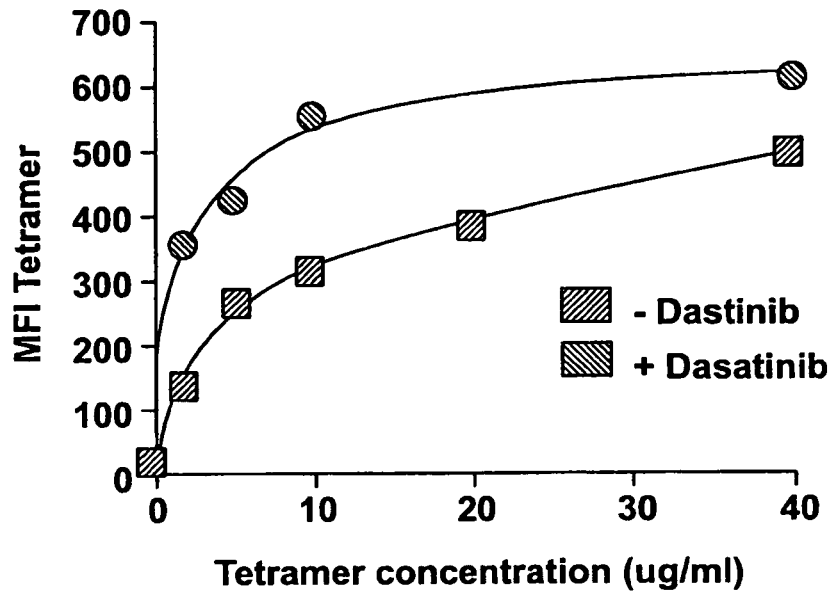
Figure 1F:
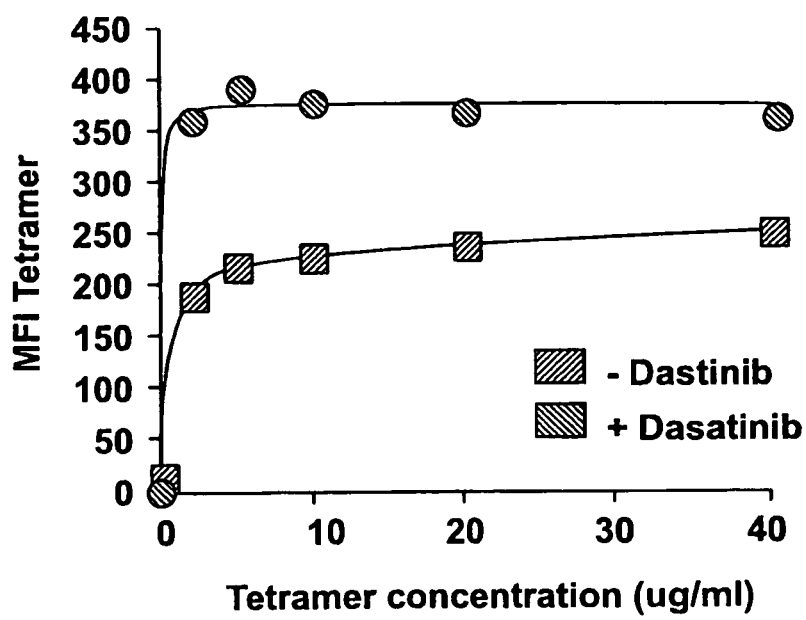
Figure 1G:
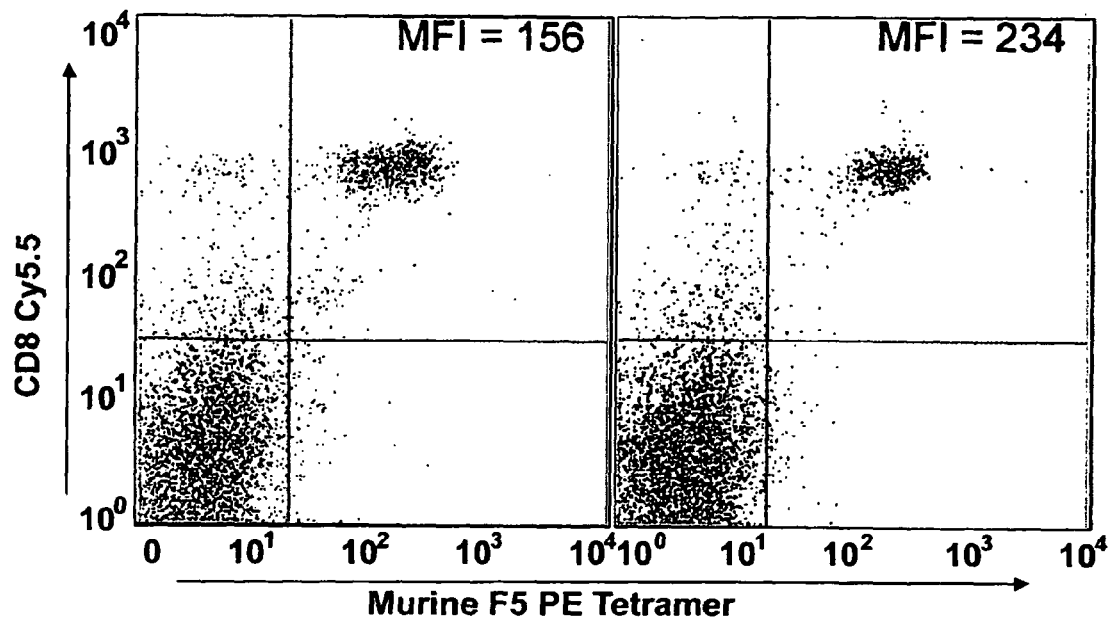
Figure 1H:
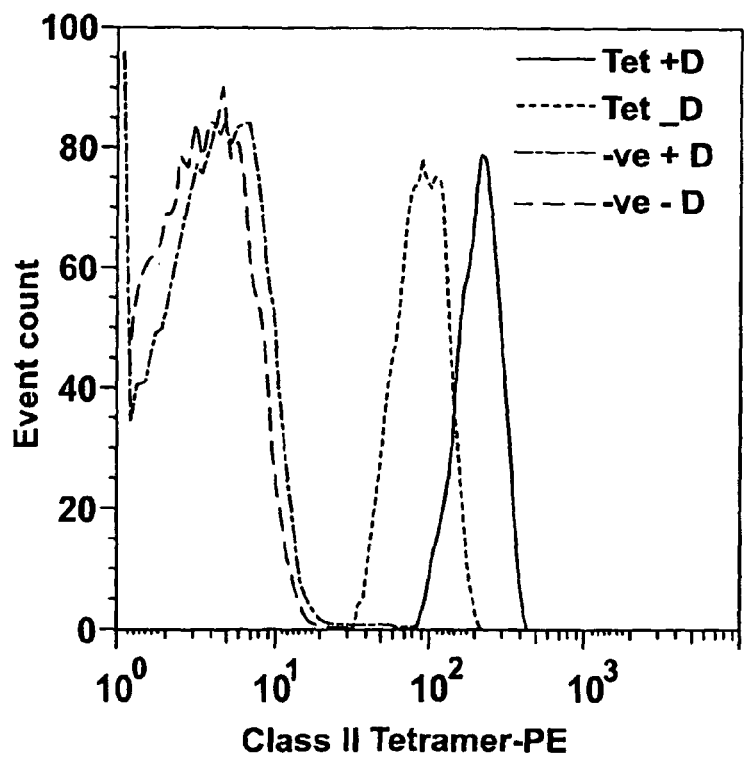

The enhancement of pMHCI tetramer staining following dasatinib treatment was highly dose dependent (FIG. 1C). Maximal effect was achieved by exposing CTL to 50 nM dasatinib for 1 hour, which resulted in an 89% increase in pMHCI tetramer staining intensity (FIG. 1C). Unexpectedly, pre-incubation of CTL with 50 nM dasatinib for as little as 30 seconds resulted in a 60% increase in pMHCI tetramer staining (FIG. 1D). Furthermore, incubation with 50 nM dasatinib for 30 minutes significantly enhanced the staining of both ILA1 and Mel13 CTL over a wide range of pMHCI tetramer concentrations (FIGS. 1E & F). Pre-incubation with dasatinib also enhanced pMHCI tetramer staining of naïve murine F5 TCR CTL directly ex vivo (FIG. 1G) and pMHCII tetramer staining of a HLA DR*010-restricted $CD4^+$ T-cell clone (FIG. 1H). Thus, pre-incubation with 50 nM dasatinib for 30 minutes provides a quick and easy way to enhance pMHC tetramer staining efficiency in both human ($CD4^+$ and $CD8^+$ T-cells) and murine systems. These effects are highly specific; increased pMHC tetramer binding only occurs in the presence of a cognate TCR/pMHC interaction (FIGS. 1B & H).

Figure 2A:
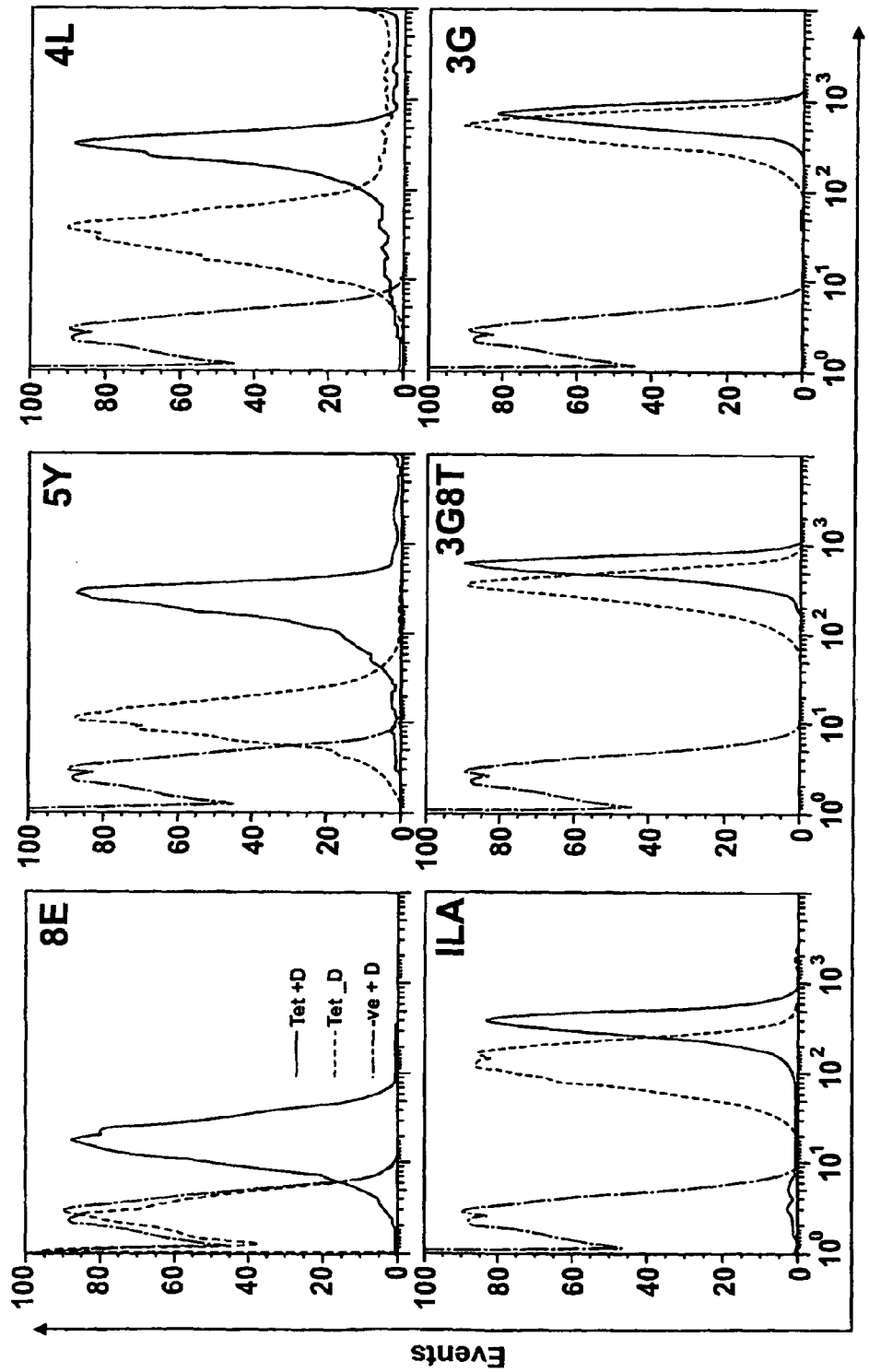
Figure 2B:
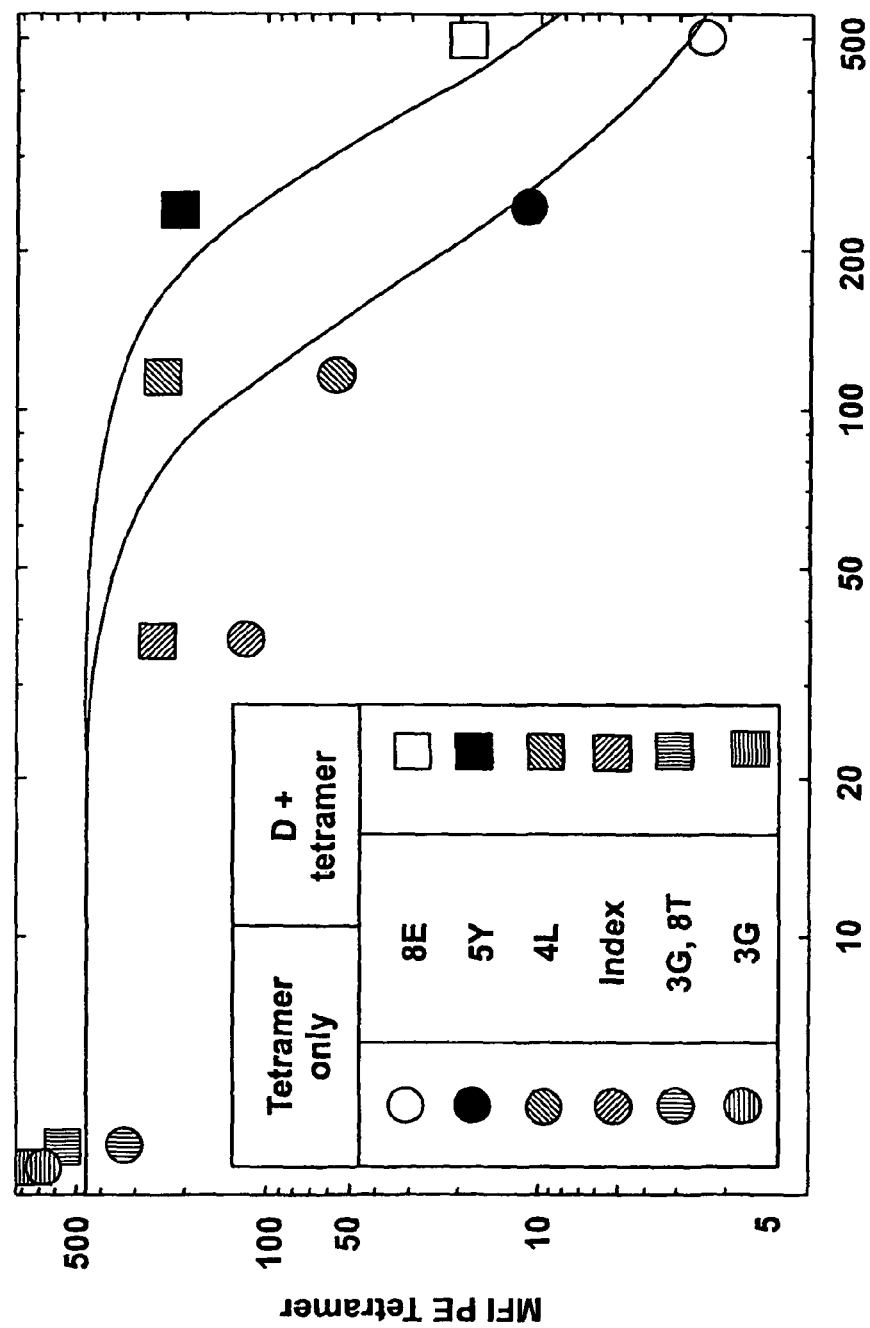

3.2 Dasatinib Preferentially Enhances pMHCI Staining of T-Cells Bearing Low Affinity TCRs In order to dissect further the effects of dasatinib, we examined pMHCI tetramer staining using several altered peptide ligands for the ILA1 CTL clone that differ in their binding affinity for the ILA1 TCR by >100-fold (Table 1). Pre-incubation with dasatinib enhanced staining efficiency with all variant pMHCI tetramers (FIG. 2A). The percentage increase in tetramer staining afforded by pre-incubation with dasatinib for 8E, 5Y, 4L, ILA index, 3G8T and 3G pMHCI tetramers was 675%, 1825%, 324%, 111%, 75% and 26%, respectively. Thus, the benefits of dasatinib pre-treatment in terms of enhanced tetramer staining intensity are greater for peptide variants that exhibit weaker interactions with the ILA1 TCR. The intensity of pMHCI tetramer staining in the presence and absence of dasatinib treatment was plotted against the monomeric TCR/pMHCI dissociation constants and a curve fitted according to the mathematical model outlined in the Materials and Methods (FIG. 2B). The data demonstrate that, in the absence of dasatinib, there is a sharp reduction in tetramer staining intensity for ligands with TCR/pMHCI $K_D$>35 µM; this is consistent with previous observations (Laugel et al., 2007). In the presence of dasatinib, however, the TCR/pMHCI affinity threshold for this sharp drop-off did not occur until the $K_D$ exceeded 200 µM. In fact, dasatinib treatment allows detectable staining of the ILA1 clone even when the agonist TCR/pMHCI $K_D$ exceeds 500 µM. Dasatinib treatment therefore enables the physical detection of CTL bearing TCRs with low affinity for the cognate pMHCI ligand that would otherwise be undetectable using pMHCI tetramer staining alone.

3.3 Dasatinib Reduces pMHCI Tetramer-Induced Cell Death

Previous studies have shown that soluble pMHCI tetramer-induced signalling can trigger cell death (Purbhoo et al., 2001; Xu et al., 2001; Guillaume et al., 2003; Cebecauer et al., 2005). This can reduce the number of live cells that remain after pMHCI tetramer staining under normal conditions. Dasatinib blocks antigen-specific signalling and subsequent T-cell effector functions (Weischel et al., 2008). Consequently, we hypothesized that dasatinib could prevent pMHCI tetramer-induced cell death. Indeed, the percentage of tetramer-positive cells that died when PBMCs were stained directly ex vivo with pMHCI tetramers representing epitopes derived from cytomegalovirus (CMV) and Epstein-Barr virus (EBV) was reduced in the presence of dasatinib (FIG. 3). Therefore, dasatinib exerts three beneficial effects: (i) it increases the intensity of pMHCI and pMHCII tetramer staining; (ii) it preferentially enhances pMHCI tetramer staining of T-cells bearing low affinity TCRs; and, (iii) it reduces pMHCI tetramer-induced cell death.

Figure 4A:
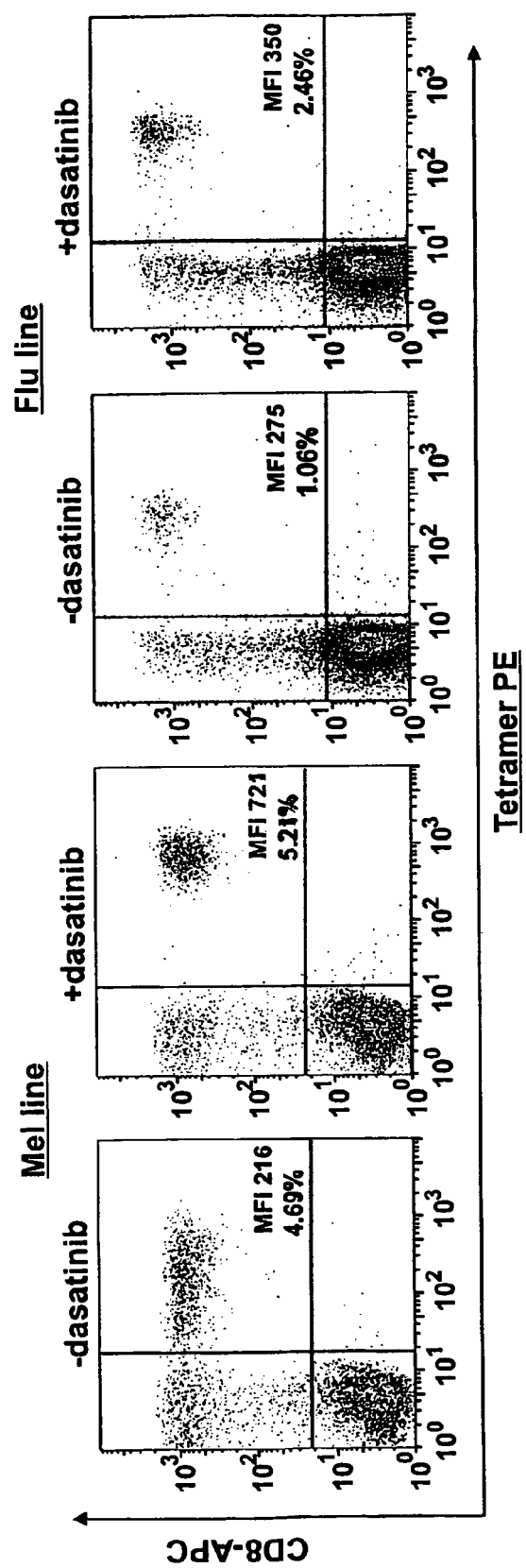
Figure 4B:
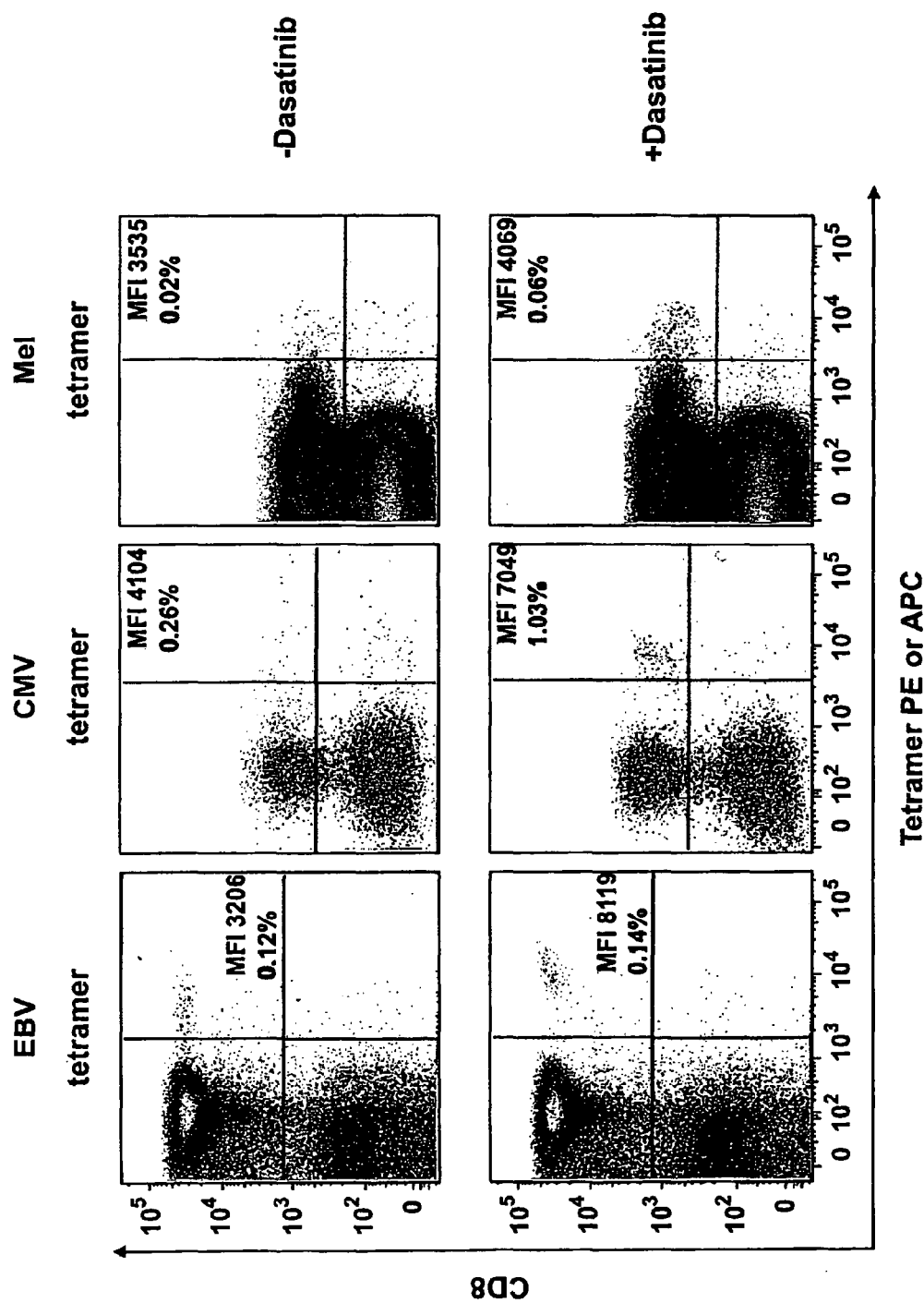

3.4 Substantial Improvements in the Detection of Antigen-Specific $CD8^+$ T-Cells Directly Ex Vivo The above findings suggest that dasatinib treatment might enable the identification of low avidity antigen-specific $CD8^+$ T-cells directly ex vivo that cannot be 'seen' in the absence of the drug. To test this idea, we first examined the staining of CTL lines in the presence or absence of 50 nM dasatinib. Staining improvements were observed in three different CTL lines raised against the Melan-A/Mart-$1_{26-35}$ epitope (ELAGIGILTV(SEQ ID NO:2)) and three different CTL lines stimulated with the influenza matrix $M1_{58-66}$ epitope (GILGFVFTL(SEQ ID NO:50)), all derived from HLA $A2^+$ individuals. Representative data are shown in FIG. 4A. In all cases, dasatinib treatment substantially enhanced the staining intensity of cognate $CD8^+$ T-cells without concomitant increases in the tetramer-negative population. In accordance with the results above, $CD8^+$ T-cells that stained poorly with pMHCI tetramer exhibited the greatest benefit from dasatinib treatment. The staining intensity of all cognate $CD8^+$ T-cells increased by at least 2-fold after dasatinib treatment, but T-cells that bound tetramer weakly exhibited increases of >20-fold in their fluorescence intensity. In many cases, larger populations of cells that stained with the corresponding pMHCI tetramer were detected after dasatinib treatment. This increase in tetramer+ cells after dasatinib treatment likely reflects the combined effects of a lower detection threshold in terms of TCR/pMHCI affinity and the fact that dasatinib reduces pMHCI tetramer-induced cell death (FIG. 3). Subsequently, we examined whether dasatinib could enhance pMHCI tetramer staining of cognate CD8+ T-cells in direct ex vivo PBMC samples and enable the detection of antigen-specific CD8+ T-cells that are 'invisible' with routine staining procedures. Indeed, a substantial increase in both pMHCI staining intensity and the percentage of antigen-specific CD8+ T-cells was observed at both 4° C. and 37° C. in PBMC samples stained with HLA A2 tetramers specific for antigens derived from CMV, EBV and Melan A (FIG. 4B).

3.5 pMHCI Staining of Functional Autoimmune CTL Following Dasatinib Treatment

Figure 5C:
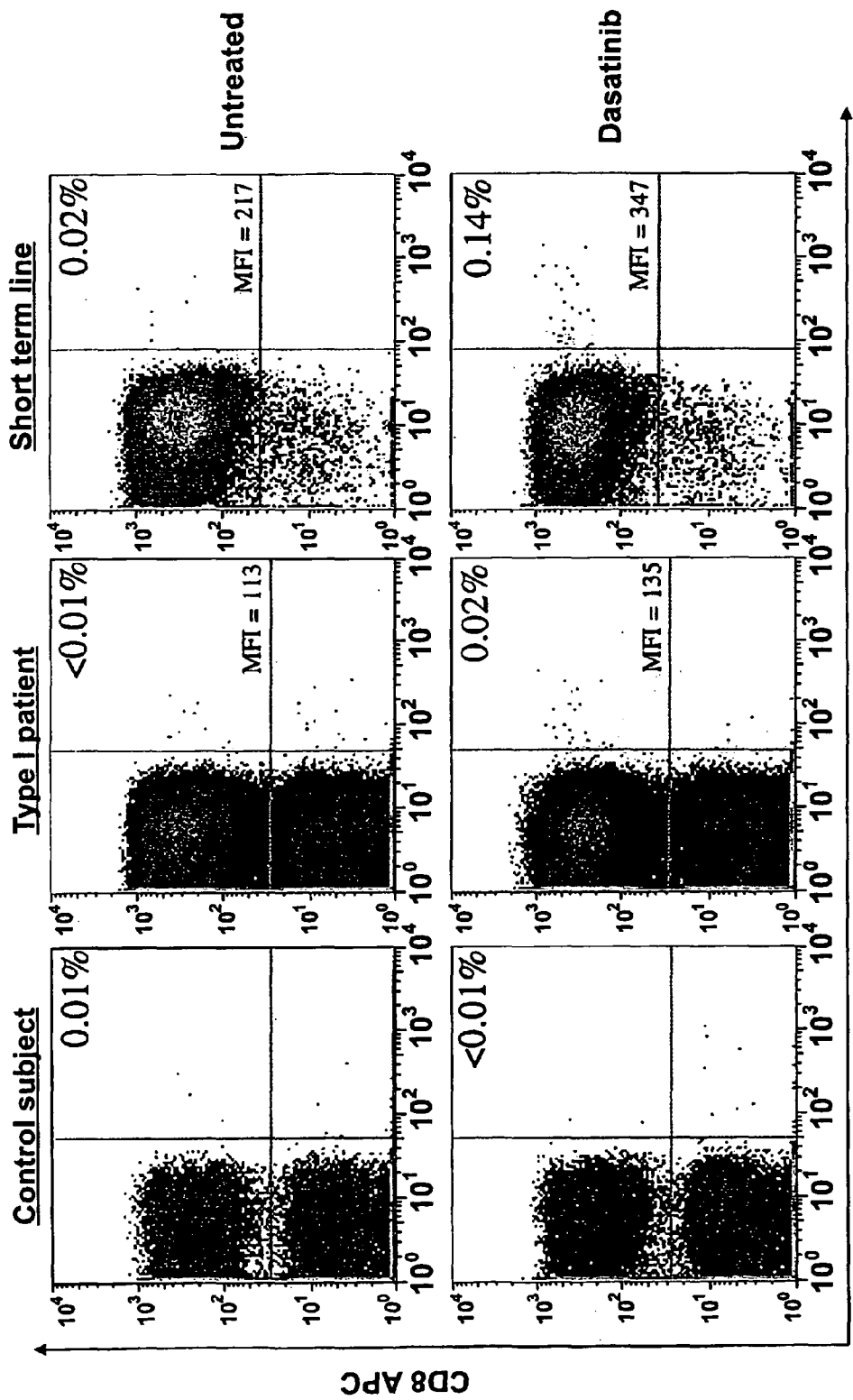

We next examined pMHCI tetramer staining of 1E6, a preproinsulin ($PPI_{15-24}$)-specific HLA A2-restricted autoreactive CTL clone isolated from a patient with type 1 diabetes. This CTL clone produces TNFα, IFNγ and MIP1β on stimulation with target cells pulsed with cognate PPI-derived peptide antigen (FIG. 5A), and does not stain with cognate pMHCI tetramer using conventional staining procedures (FIG. 5B). An identical result was obtained for 2D6, a different PPI-specific CTL clone isolated from a patient with type I diabetes (data not shown). Dasatinib treatment allowed both CTL clones to bind cognate tetramer without affecting staining with non-cognate tetramer (FIG. 5B & data not shown). In keeping with these findings, dasatinib treatment allowed the identification of a HLA A2/$PPI_{15-24}$ tetramer-positive population directly ex vivo from a type I diabetic patient, consistent with a corresponding IFNγ ELISpot response to $PPI_{15-24}$ peptide of 13 responder cells per $10^6$ PBMCs (FIG. 5C & data not shown). Dasatinib did not increase direct ex vivo HLA A2/$PP1_{15-24}$ tetramer staining in healthy HLA A2-matched control subjects (FIG. 5C). A seven-fold increase in the percentage of autoreactive CTL was observed when short-term lines expanded from two type I diabetic patients were stained in the presence of dasatinib (FIG. 5C & data not shown). Thus, dasatinib treatment allows the detection of functional autoreactive CTL that are otherwise undetectable with standard staining conditions.

3.6 How does Dasatinib Exert its Beneficial Effects on pMHC Tetramer Staining?

Previous studies have demonstrated that incubation with Src kinase inhibitors results in enhanced TCR and CD8 expression at the cell surface (Luton et al., 1994; D'Oro et al., 1997). Consistent with these observations, we have recently demonstrated that increased levels of TCR and CD8 are seen at the cell surface following incubation with dasatinib for 4 hours (Weischel et al., 2008). Initially, therefore, we investigated this increase in TCR and CD8 levels as a possible mechanism for the observed effects on tetramer binding. The beneficial effects of dasatinib on pMHCI tetramer staining were observed within seconds of dasatinib treatment (FIG. 1D), whereas significant increases in TCR and CD8 levels were not observed until >30 minutes (FIG. 6). Therefore, this time dependent accumulation of TCR and CD8 at the cell surface cannot explain the effects of dasatinib on tetramer binding.

We next investigated whether the mechanism of PKI action operates through TCR- or CD8-mediated effects. Dasatinib treatment enhanced pMHCI tetramer staining of the HLA A2-restricted ELAGIGILTV (SEQ ID NO:2)-specific Melc5 CTL clone and a CTL line raised against the MeIan-A/Mart-$1_{26-35}$ epitope (ELAGIGILTV(SEQ ID NO:2) with both wild-type and CD8-null (DT227/8KA) tetramers (FIGS. 7A & B), thereby demonstrating that PKIs can exert their effects in the absence of a pMHCI/CD8 interaction. Thus, consistent with effects on pMHCII tetramer binding (FIG. 1), dasatinib does not enhance pMHCI tetramer binding via CD8-mediated effects.

Figure 8B:
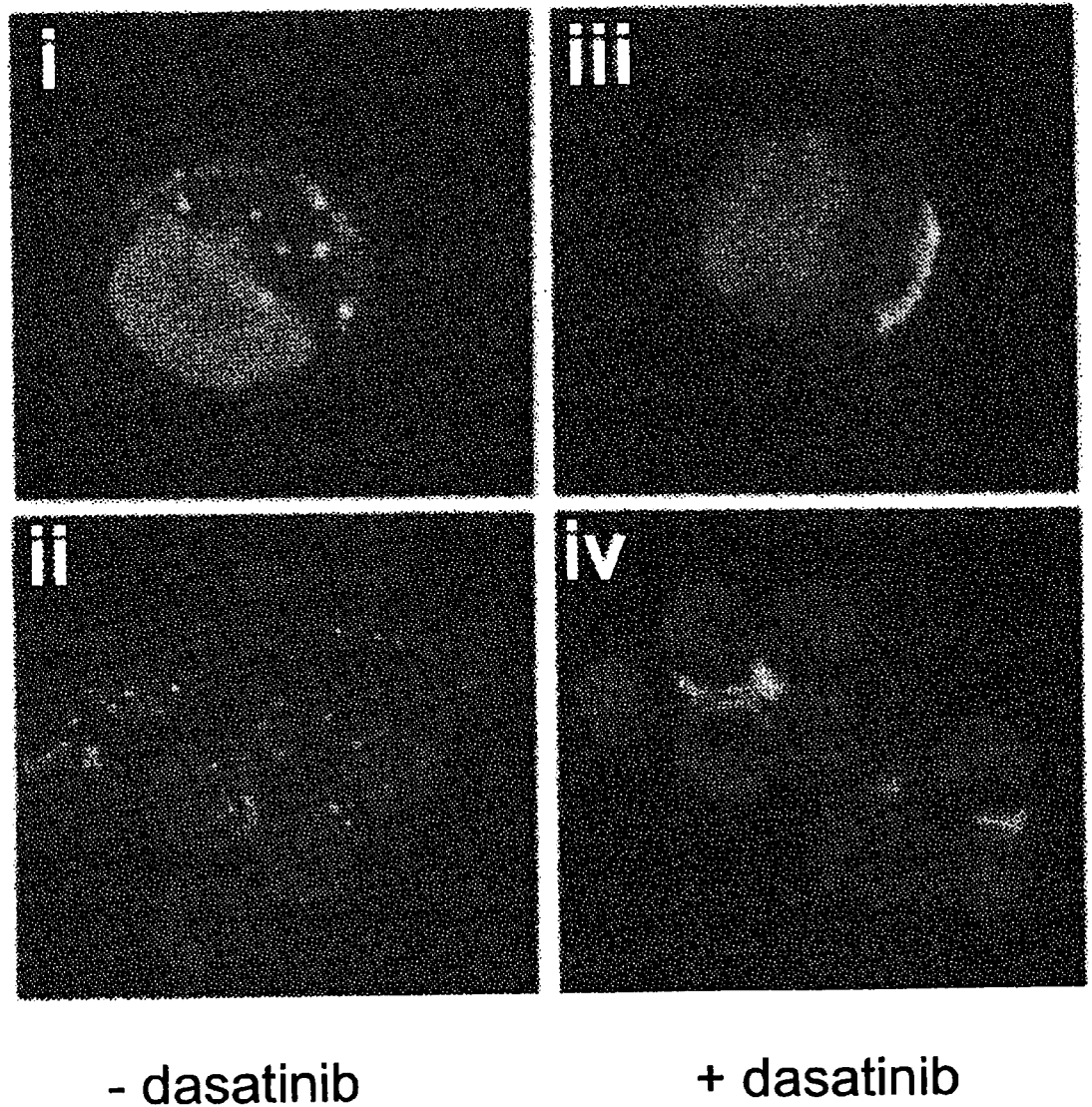

TCR expression levels are not static and TCRs are constantly being down-regulated from the cell surface (Krangel, 1987). TCR internalization is thought to be mediated by three different mechanisms: (i) constitutive recycling of the TCR between intracellular compartments and the plasma membrane in resting cells by an unknown mechanism (Dietrich et al., 2002); (ii) protein kinase C activation (Minami et al., 1987; Dietrich et al., 2002); and, (iii) lck-mediated tyrosine phosphorylation following TCR ligation by specific pMHCI ligand. Dasatinib has been shown to target lck and therefore has the potential to inhibit the latter pathway of TCR down-regulation. Indeed, dasatinib treatment was found to block antigen-induced TCR downregulation from the CTL surface (FIG. 8A). pMHC tetramers are rapidly internalized under normal staining conditions (Whelan et al., 1999) and therefore we reasoned that dasatinib might exert its beneficial effects by blocking this process. To this end, fluorescence microscopy was performed in the presence and absence of dasatinib (FIG. 8B). HLA A2/ILAKFLHWL (SEQ ID NO:1)-Alexa488 tetramer capping and internalization was blocked in the presence of dasatinib and remained on the cell surface where it formed a ring that was visibly brighter than tetramer that had been internalized (FIG. 8B). Thus, by preventing TCR downregulation, PK inhibition acts to drive the system towards a higher number of surface TCRs and a higher number of potential productive engagements with pMHC tetramer. This has the effect of increasing tetramer on-rate, at least in pMHCI systems (FIG. 9).

4. Discussion pMHC tetramer technology has revolutionized the study of antigen specific T-cells. However, one major limitation of this technique is that pMHCI, and most likely pMHCII, tetramer staining is dependent on a distinct TCR affinity threshold (Laugel et al., 2007). Consequently, pMHC tetramers fail to identify T-cells that express TCRs with low affinity for cognate antigen; such low affinity interactions characterize TCR/pMHCI binding in tumor-specific and autoreactive CD8+ T-cells (Cole et al., 2007). Here, we demonstrate that a short incubation with a reversible PKI such as dasatinib results in three major benefits in terms of pMHC tetramer staining. First, substantial improvements in pMHC tetramer staining intensity are observed. This effect applies to both CD4+ and CD8+ T-cells (FIG. 1). Indeed, the beneficial effects are so striking even at low pMHC tetramer concentrations that dasatinib treatment could be used to conserve reagent. Second, dasatinib treatment reduces tetramer-induced cell death that has been previously reported to be an issue with pMHCI tetramer staining protocols (Purbhoo et al., 2001; Xu et al., 2001; Guillaume et al., 2003; Cebecauer et al., 2005). Third, the benefits of dasatinib treatment are greater for TCR/pMHCI interactions of weak affinity and, as a result, dasatinib enhances the detection of low avidity CD8+ T-cells; this effect increases the number of CD8+ T-cells that can be detected directly ex vivo, particularly in the setting of tumor-specific and autoreactive CD8+ T-cell populations. Such effects are also likely to apply to CD4+ T-cells, which typically bind cognate pMHCII antigens with affinities lower than those reported for pMHCI systems (Cole et al., 2007).

Importantly, no increase in background staining was seen in any of the systems tested here (FIGS. 1B, 1H, 5B & 5C). In fact the tetramer negative background was actually seen to decrease with dasatinib treatment in some staining experiments (FIGS. 4C & 5C). Dasatinib proved to be a particularly powerful tool in the detection of autoreactive CTL from type I diabetic patients. No increase in the PPI tetramer positive population was observed in healthy donors and indeed staining was only ever seen if a functional response to the preproinsulin peptide was evident. Therefore benefits only apply to T-cells that express TCRs specific for the pMHCI tetramer in use. This conclusion is further strengthened by the finding that the beneficial effects are TCR mediated and do not involve the CD8 coreceptor. Therefore dasatinib facilitates the specific TCR/pMHCI interaction rather, than the non-specific pMHCI/CD8 interaction.

Dasatinib prevents TCR downregulation and tetramer internalization from the cell surface. How does this effect result in faster tetramer on-rates and the beneficial effects described above? When an individual pMHC molecule in a pMHC tetramer engages a cell surface TCR, this engagement can be either 'productive' or 'non-productive' in terms of capturing the tetramer from solution (FIG. 10). A productive engagement requires a second pMHC in the tetramer to bind a second TCR before the first pMHC dissociates. By preventing TCR downregulation after non-productive engagement, dasatinib treatment acts to maintain TCRs on the cell surface where they are available for future interactions. There is increasing evidence that non-triggered TCRs are internalized with engaged TCRs (Niedergang et al., 1997; San. Jose et al., 2000). Thus, it is possible that the tetramer internalization that occurs after productive engagement in the absence of dasatinib treatment also results in the internalization of non-engaged TCR and coreceptor. By preventing TCR downregulation, dasatinib and other effective PKIs would act to maintain surface TCRs and therefore enable a higher number of potential productive engagements with pMHC tetramer as indicated by the red arrows (FIG. 10).

In summary, we have demonstrated that a short incubation with reversible PKIs such as dasatinib substantially improves the staining intensity of cognate T-cells with pMHC tetramers and can expose concealed antigen-specific T-cells that bear low affinity TCRs. These benefits are restricted to cognate T-cells and are not accompanied by concomitant increases in background staining. This simple and universally applicable technique is likely to be beneficial in all studies of antigen-specific T-cells.

REFERENCES

Altman, J. D., Moss, P. A., Goulder, P. J., Barouch, D. H., McHeyzer-Williams, M. G., Bell, J. I., McMichael, A. J. and Davis, M. M. (1996) Phenotypic analysis of antigen-specific T lymphocytes. Science 274, 94-6.

Arif, S., Tree, T. I., Astill, T. P., Tremble, J. M., Bishop, A. J., Dayan, C. M., Roep, B. O. and Peakman, M. (2004) Autoreactive T cell responses show proinflammatory polarization in diabetes but a regulatory phenotype in health. J. Clin. Invest. 113, 451-63.

Burrows, S. R., Kienzle, N., Winterhalter, A., Bharadwaj, M., Altman, J. D. and Brooks, A. (2000) Peptide-MHC class I tetrameric complexes display exquisite ligand specificity. J. Immunol. 165, 6229-34.

Carter, T. A., Wodicka, L. M., Shah, N. P., Velasco, A. M., Fabian, M. A., Treiber, D. K., Milanov, Z. V., Atteridge, C. E., Biggs, W. H., 3rd, Edeen, P. T., Floyd, M., Ford, J. M., Grotzfeld, R. M., Herrgard, S., Insko, D. E., Mehta, S. A., Patel, H. K., Pao, W., Sawyers, C. L., Varmus, H., Zarrinkar, P. P. and Lockhart, D. J. (2005) Inhibition of drug-resistant mutants of ABL, KIT, and EGF receptor kinases. Proc. Natl. Acad. of Sci. 102, 11011-6.

Cebecauer, M., Guillaume, P., Hozak, P., Mark, S., Everett, H., Schneider, P. and Luescher, I. F. (2005) Soluble MHC-peptide complexes induce rapid death of CD8+ CTL. J. Immunol. 174, 6809-19.

Chang, L., Kjer-Nielsen, L., Flynn, S., Brooks, A. G., Mannering, S. I., Honeyman, M. C., Harrison, L. C., McCluskey, J. and Purcell, A. W. (2003) Novel strategy for identification of candidate cytotoxic T-cell epitopes from human preproinsulin. Tissue Antigens 62, 408-17.

Chattopadhyay, P. K., Price, D. A., Harper, T. F., Betts, M. R., Yu, J., Gostick, E., Perfetto, S. P., Goepfert, P., Koup, R. A., De Rosa, S. C., Bruchez, M. P. and Roederer, M. (2006) Quantum dot semiconductor nanocrystals for immunophenotyping by polychromatic flow cytometry. Nat. Med. 12, 972-7.

Cole, D. K., Pumphrey, N. J., Boulter, J. M., Sami, M., Bell, J. I., Gostick, E., Price, D. A., Gao, G. F., Sewell, A. K. and Jakobsen, B. K. (2007) Human TCR-binding affinity is governed by MHC class restriction. J. Immunol. 178, 5727-34.

D'Oro, U., Vacchio, M. S., Weissman, A. M. and Ashwell, J. D. (1997) Activation of the Lck tyrosine kinase targets cell surface T cell antigen receptors for lysosomal degradation. Immunity 7, 619-28.

Dietrich, J., Menne, C., Lauritsen, J. P., von Essen, M., Rasmussen, A. B., Odum, N. and Geisler, C. (2002) Ligand-induced TCR down-regulation is not dependent on constitutive TCR cycling. J. Immunol. 168, 5434-40.

Guillaume, P., Legler, D. F., Boucheron, N., Doucey, M. A., Cerottini, J. C. and Luescher, I. F. (2003) Soluble Major Histocompatibility Complex-Peptide Octamers with Impaired CD8 Binding Selectively Induce Fas-dependent Apoptosis. J. Biol. Chem. 278, 4500-9.

Hutchinson, S. L., Wooldridge, L., Tafuro, S., Laugel, B., Glick, M., Boulter, J. M., Jakobsen, B. K., Price, D. A. and Sewell, A. K. (2003) The CD8 T cell coreceptor exhibits disproportionate biological activity at extremely low binding affinities. J Biol Chem 278, 24285-93.

Krangel, M. S. (1987) Endocytosis and recycling of the T3-T cell receptor complex. The role of T3 phosphorylation. J. Exp. Med. 165, 1141-59.

Laugel, B., Boulter, J. M., Lissin, N., Vuidepot, A., Li, Y., Gostick, E., Crotty, L. E., Douek, D. C., Hemelaar, J., Price, D. A., Jakobsen, B. K. and Sewell, A. K. (2005) Design of soluble recombinant T cell receptors for antigen targeting and T cell inhibition. J. Biol. Chem. 280, 1882-92.

Laugel, B., van den Berg, N. A., Gostick, E., Cole, D. K., Wooldridge, L., Boulter, J. M., Milicic, A., Price, D. A. and Sewell, A. K. (2007) Different T cell receptor affinity thresholds and CD8 coreceptor dependency govern cytotoxic T lymphocyte activation and tetramer binding properties. J. Biol. Chem. 282, 23799-2381.

Lombardo, L. J., Lee, F. Y., Chen, P., Norris, D., Barrish, J. C., Behnia, K., Castaneda, S., Cornelius, L. A., Das, J., Doweyko, A. M., Fairchild, C., Hunt, J. T., Inigo, I., Johnston, K., Kamath, A., Kan, D., Klei, H., Marathe, P., Pang, S., Peterson, R., Pitt, S., Schieven, G. L., Schmidt, R. J., Tokarski, J., Wen, M. L., Wityak, J. and Borzilleri, R. M. (2004) Discovery of N-(2-chloro-6-methyl-phenyl)-2-(6-(4-(2-hydroxyethyl)-piperazin-1-yl)-2-methylpyrimidin-4-ylamino)thiazole-5-carboxamide (BMS-354825), a dual Src/Abl kinase inhibitor with potent antitumor activity in preclinical assays. J. Med. Chem. 47, 6658-61.

Luton, F., Buferne, M., Davoust, J., Schmitt-Verhulst, A. M. and Boyer, C. (1994) Evidence for protein tyrosine kinase involvement in ligand-induced TCR/CD3 internalization and surface redistribution. J. Immunol. 153, 63-72.

Magnusson, M. K., Meade, K. E., Nakamura, R., Barrett, J. and Dunbar, C. E. (2002) Activity of STI571 in chronic myelomonocytic leukemia with a platelet-derived growth factor beta receptor fusion oncogene. Blood 100, 1088-91.

Mamalaki, C., Elliott, J., Norton, T., Yannoutsos, N., Townsend, A. R., Chandler, P., Simpson, E. and Kioussis, D. (1993) Positive and negative selection in transgenic mice expressing a T-cell receptor specific for influenza nucleoprotein and endogenous superantigen. Develop. Immunol. 3, 159-74.

Melenhorst, J. J., Scheinberg, P., Lissina, A., Chattopadhyay, P. K., Gostick, E., Cole, D. K., Wooldridge, L., van den Berg, H. A., Bornstein, E., Hensel, N. F., Douek, D. C., Roederer, M., Sewell, A., K., Barrett, J. and Price, D. A. (2008) Detection of low avidity CD8+ T cells with core-ceptor-enhanced peptide-MHC class I tetramers. J. Immunol. Methods (In Press)

Minami, Y., Samelson, L. E. and Klausner, R. D. (1987) Internalization and cycling of the T cell antigen receptor. Role of protein kinase C. J. Biol. Chem. 262, 13342-7.

Niedergang, F., Dautry-Varsat, A. and Alcover, A. (1997) Peptide antigen or superantigen-induced down-regulation of TCRs involves both stimulated and unstimulated receptors. J. Immunol. 159, 1703-10.

Purbhoo, M. A., Boulter, J. M., Price, D. A., Vuidepot, A. L., Hourigan, C. S., Dunbar, P. R., Olson, K., Dawson, S. J., Phillips, R. E., Jakobsen, B. K., Bell, J. I. and Sewell, A. K. (2001) The human CD8 coreceptor effects cytotoxic T cell activation and antigen sensitivity primarily by mediating complete phosphorylation of the T cell receptor zeta chain. J. Biol. Chem. 276, 32786-92.

San Jose, E., Borroto, A., Niedergang, F., Alcover, A. and Alarcon, B. (2000) Triggering the TCR complex causes the downregulation of nonengaged receptors by a signal transduction-dependent mechanism. Immunity 12, 161-70.

Shah, N. P., Tran, C., Lee, F. Y., Chen, P., Norris, D. and Sawyers, C. L. (2004) Overriding imatinib resistance with a novel ABL kinase inhibitor. Science 305, 399-401.

van den Berg, H. A., Wooldridge, L., Laugel, B. and Sewell, A. K. (2007) Coreceptor CD8-driven modulation of T cell antigen receptor specificity. J. Theor. Biol. 249, 395-408.

Weichsel, R., Dix, C., Wooldridge, L., Clement, M., Fenton-May, A., Sewell, A. K., Zezula, J., Greiner, E., Gostick, E., Price, D. A., Einsele, H. and Seggewiss, R. (2008) Profound inhibition of antigen-specific T-cell effector functions by dasatinib. Clin. Cancer Res. 14, 2484-91.

Whelan, J. A., Dunbar, P. R., Price, D. A., Purbhoo, M. A., Lechner, F., Ogg, G. S., Griffiths, G., Phillips, R. E., Cerundolo, V. and Sewell, A. K. (1999) Specificity of CTL interactions with peptide-MHC class I tetrameric complexes is temperature dependent. J. Immunol. 163, 4342-8.

Wooldridge, L., van den Berg, H. A., Glick, M., Gostick, E., Laugel, B., Hutchinson, S. L., Milicic, A., Brenchley, J. M., Douek, D. C., Price, D. A. and Sewell, A. K. (2005) Interaction between the CD8 coreceptor and major histocompatibility complex class I stabilizes T cell receptor-antigen complexes at the cell surface. J. Biol. Chem. 280, 27491-501.

Xu, X. N., Purbhoo, M. A., Chen, N., Mongkolsapaya, J., Cox, J. H., Meier, U. C., Tafuro, S., Dunbar, P. R., Sewell, A. K., Hourigan, C. S., Appay, V., Cerundolo, V., Burrows, S. R., McMichael, A. J. and Screaton, G. R. (2001) A novel approach to antigen-specific deletion of CTL with minimal cellular activation using alpha3 domain mutants of MHC class I/peptide complex. Immunity 14, 591-602.

TABLE ONE

Table 1: Affinity measurements of the interaction between the ILA1 TCR and hTERT$_{540-548}$ pMHCI variants.

| | LIGAND | | | | | | |
|---|---|---|---|---|---|---|---|
| | 8E | 5Y | 4L | index | 8Y | 3G8T | 3G |
| $K_D$ ILA1 TCR Binding (μM) | >500 | 242 | 117 | 36.6 | 22.6 | 4.04 | 3.7 |

Summary of the results obtained by nonlinear analysis of surface plasmon resonance binding equilibrium experiments as detailed in Laugel et al. 2007 (Laugel et al., 2007) and Melenhorst et al (Melenhorst et al., 2008).
$K_D$ values were determined by analyzing the data in nonlinear curve fittings to the equation $AB = B \times AB_{max}/(K_D + B)$ assuming 1:1 Langmuir binding.

The invention claimed is:

1. A method for enhanced detection, within a population of cells, of T cells of the immune system, comprising:

exposing said population of cells to at least one Lck tyrosine kinase inhibitor either before, or whilst, exposing said population of cells to at least one peptide MHC multimer that detects or stains Lck tyrosine kinase sensitive T cell surface receptors, wherein said population of cells is exposed to said inhibitor for up to three hours.

2. A method of conserving peptide MHC staining agents when detecting, within a population of cells, T cells of the immune system, comprising:

exposing said population of cells to at least one Lck tyrosine kinase inhibitor either before, or whilst, exposing said population of cells to at least one peptide MHC multimer that detects or stains Lck tyrosine kinase sensitive T cell surface receptors, wherein said population of cells is exposed to said inhibitor for up to three hours, thereby enhancing detection of said T cell surface receptors by said peptide MHC multimer.

3. A method of sorting, in a population of cells, a viable, selected, sub-population of T cells, comprising:

exposing said population of cells to at least one Lck tyrosine kinase inhibitor either before, or whilst, exposing said population of cells to at least one peptide MHC multimer that detects or stains a selected type of T cell and thereby enables said selected T cells to be sorted, detected or stained and simultaneously, or subsequently, isolated from said population of cells; wherein exposure of said population of cells to said Lck tyrosine kinase inhibitor increases the viability of said selected T cells relative to said selected T cells not exposed to said Lck tyrosine kinase inhibitor; and sorting said selected T cells stained by said at least one peptide MHC multimer.

4. The method of claim 1, wherein said Lck tyrosine kinase inhibitor is a reversible Lck tyrosine kinase inhibitor such that its binding action to its target site or substrate can be reversed.

5. The method of claim 1, wherein said Lck tyrosine kinase inhibitor is Dasatinib or Lck inhibitor II.

6. The method of claim 1, wherein said peptide MHC multimer is a peptide MHC class I and /or a peptide MHC class II multimer.

7. The method of claim 1, wherein exposing said population of cells to said inhibitor comprises exposing for a period of time up to one hour.

8. The method of claim 7, wherein said period is approximately 30 minutes.

9. The method of claim 1 wherein said Lck tyrosine kinase inhibitor is used at a concentration of up to 300nM.

10. The method of claim 9, wherein said concentration is less than 200 nM.

11. The method of claim 1, wherein the peptide MHC multimer is a tetramer, pentamer, octomer or dextramer.

12. The method according to claim 1, wherein said Lck tyrosine kinase inhibitor exposure increases the overall avidity for peptide MHC multimer.

* * * * *